(12) United States Patent
Grosman et al.

(10) Patent No.: US 11,694,784 B2
(45) Date of Patent: *Jul. 4, 2023

(54) INFUSION SYSTEMS AND RELATED PERSONALIZED BOLUSING METHODS

(71) Applicant: MEDTRONIC MINIMED, INC., Northridge, CA (US)

(72) Inventors: Benyamin Grosman, Valley Village, CA (US); Anirban Roy, Agoura Hills, CA (US); Patrick E. Weydt, Moorpark, CA (US); Neha J. Parikh, West Hills, CA (US); Louis J. Lintereur, Stevenson Ranch, CA (US); Di Wu, Glendale, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 323 days.

This patent is subject to a terminal disclaimer.

(21) Appl. No.: 17/080,481

(22) Filed: Oct. 26, 2020

(65) Prior Publication Data

US 2021/0043299 A1 Feb. 11, 2021

Related U.S. Application Data

(63) Continuation of application No. 15/847,755, filed on Dec. 19, 2017, now Pat. No. 10,854,323.
(Continued)

(51) Int. Cl.
*G16H 20/17* (2018.01)
*A61B 5/00* (2006.01)
(Continued)

(52) U.S. Cl.
CPC ......... *G16H 20/17* (2018.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS

| 4,562,751 A | 1/1986 | Nason et al. |
| 4,685,903 A | 8/1987 | Cable et al. |
| (Continued) | | |

FOREIGN PATENT DOCUMENTS

| WO | 2011030343 A1 | 3/2011 |
| WO | 2018064222 A1 | 4/2018 |

OTHER PUBLICATIONS

European Examination Report issued in corresponding Application No. EP 17829531.7 dated Mar. 11, 2021 (4 pages).

*Primary Examiner* — Manuel A Mendez
(74) *Attorney, Agent, or Firm* — Weaver Austin Villeneuve & Sampson LLP

(57) ABSTRACT

Infusion systems, infusion devices, and related operating methods are provided. An exemplary method of operating an infusion device capable of delivering fluid to a patient involves obtaining, by a control system associated with the infusion device, an input meal indication, obtaining historical data for the patient associated with the input meal indication, determining an estimated carbohydrate amount corresponding to the input meal indication based at least in part on the historical data, determining a bolus dosage of the insulin based at least in part on the estimated carbohydrate amount, and operating an actuation arrangement of the infusion device to deliver the bolus dosage of the insulin to the patient.

20 Claims, 16 Drawing Sheets

Related U.S. Application Data

(60) Provisional application No. 62/437,536, filed on Dec. 21, 2016.

(51) Int. Cl.

| | | |
|---|---|---|
| *A61B 5/145* | (2006.01) | |
| *A61M 5/142* | (2006.01) | |
| *A61M 5/172* | (2006.01) | |
| *G16H 50/50* | (2018.01) | |
| *G16H 50/20* | (2018.01) | |
| *G16H 10/20* | (2018.01) | |
| *G16H 10/60* | (2018.01) | |
| *G16H 20/60* | (2018.01) | |
| *G16H 40/63* | (2018.01) | |
| *A61M 5/145* | (2006.01) | |
| *A61M 5/168* | (2006.01) | |
| *A61K 38/28* | (2006.01) | |
| *G16H 20/30* | (2018.01) | |
| *G16H 50/30* | (2018.01) | |

(52) U.S. Cl.
CPC ............ *A61M 5/142* (2013.01); *A61M 5/145* (2013.01); *A61M 5/14244* (2013.01); *A61M 5/16831* (2013.01); *A61M 5/1723* (2013.01); *G16H 10/20* (2018.01); *G16H 10/60* (2018.01); *G16H 20/60* (2018.01); *G16H 40/63* (2018.01); *G16H 50/20* (2018.01); *G16H 50/50* (2018.01); *A61B 5/746* (2013.01); *A61B 5/7465* (2013.01); *A61K 38/28* (2013.01); *A61M 5/16804* (2013.01); *A61M 5/16877* (2013.01); *A61M 2005/14208* (2013.01); *A61M 2205/18* (2013.01); *A61M 2205/3303* (2013.01); *A61M 2205/35* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/8206* (2013.01); *A61M 2230/201* (2013.01); *A61M 2230/63* (2013.01); *G16H 20/30* (2018.01); *G16H 50/30* (2018.01)

(56) References Cited

U.S. PATENT DOCUMENTS

| | | | |
|---|---|---|---|
| 4,755,173 A | 7/1988 | Konopka et al. | |
| 5,080,653 A | 1/1992 | Voss et al. | |
| 5,097,122 A | 3/1992 | Colman et al. | |
| 5,391,250 A | 2/1995 | Cheney, II et al. | |
| 5,485,408 A | 1/1996 | Blomquist | |
| 5,505,709 A | 4/1996 | Funderburk et al. | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Vanantwerp et al. | |
| 6,017,328 A | 1/2000 | Fischell et al. | |
| 6,088,608 A | 7/2000 | Schulman et al. | |
| 6,119,028 A | 9/2000 | Schulman et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,485,465 B2 | 11/2002 | Moberg et al. | |
| 6,544,212 B2 | 4/2003 | Galley et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,589,229 B1 | 7/2003 | Connelly et al. | |
| 6,591,876 B2 | 7/2003 | Safabash | |
| 6,641,533 B2 | 11/2003 | Causey, III et al. | |
| 6,659,980 B2 | 12/2003 | Moberg et al. | |
| 6,736,797 B1 | 5/2004 | Larsen et al. | |
| 6,740,072 B2 | 5/2004 | Starkweather et al. | |
| 6,749,587 B2 | 6/2004 | Flaherty | |
| 6,752,787 B1 | 6/2004 | Causey, III et al. | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,817,990 B2 | 11/2004 | Yap et al. | |
| 6,827,702 B2 | 12/2004 | Lebel et al. | |
| 6,932,584 B2 | 8/2005 | Gray et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,323,142 B2 | 1/2008 | Pendo et al. | |
| 7,399,277 B2 | 7/2008 | Saidara et al. | |
| 7,402,153 B2 | 7/2008 | Steil et al. | |
| 7,442,186 B2 | 10/2008 | Blomquist | |
| 7,602,310 B2 | 10/2009 | Mann et al. | |
| 7,621,893 B2 | 11/2009 | Moberg et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,474,332 B2 | 7/2013 | Bente, IV | |
| 8,674,288 B2 | 3/2014 | Hanson et al. | |
| 8,954,373 B2 | 2/2015 | Atlas et al. | |
| 9,330,237 B2 | 5/2016 | Cohen et al. | |
| 9,561,324 B2 | 2/2017 | Estes | |
| 10,252,002 B2 | 4/2019 | Haider et al. | |
| 10,854,323 B2 * | 12/2020 | Grosman | G16H 10/20 |
| 2005/0049179 A1 | 3/2005 | Davidson et al. | |

(56) References Cited

U.S. PATENT DOCUMENTS

| | | |
|---|---|---|
| 2006/0031094 A1 | 2/2006 | Cohen et al. |
| 2007/0123819 A1 | 5/2007 | Mernoe et al. |
| 2010/0160861 A1 | 6/2010 | Causey, III et al. |
| 2010/0249530 A1 | 9/2010 | Rankers et al. |
| 2010/0262434 A1 | 10/2010 | Shaya |
| 2010/0280329 A1 | 11/2010 | Randlov et al. |
| 2013/0338630 A1 | 12/2013 | Agrawal et al. |
| 2014/0066889 A1 | 3/2014 | Grosman et al. |
| 2015/0273147 A1 | 10/2015 | Duke et al. |
| 2017/0193184 A1 | 7/2017 | Hayter et al. |
| 2018/0161495 A1 | 6/2018 | Estes |
| 2022/0044784 A1 | 2/2022 | Grosman et al. |

\* cited by examiner

INFUSION SYSTEMS AND RELATED PERSONALIZED BOLUSING METHODS

CROSS-REFERENCE TO RELATED APPLICATION(S)

This application is a continuation of U.S. patent application Ser. No. 15/847,755, filed Dec. 19, 2017, which claims the benefit of U.S. Provisional Patent Application Ser. No. 62/437,536, filed Dec. 21, 2016, the entire contents of which are incorporated by reference herein.

TECHNICAL FIELD

Embodiments of the subject matter described herein relate generally to medical devices, and more particularly, embodiments of the subject matter relate to automatically adapting operations of a fluid infusion device in a personalized manner.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Regulating blood glucose level is complicated by variations in the response time for the type of insulin being used along with each user's individual insulin response. Furthermore, a user's daily activities and experiences may cause that user's insulin response to vary throughout the course of a day or from one day to the next. Thus, it is desirable to account for the anticipated variations or fluctuations in the user's insulin response caused by the user's activities or other condition(s) experienced by the user.

Managing a diabetic's blood glucose level is also complicated by the user's consumption of meals or carbohydrates. Often, a user manually administers a bolus of insulin at or around meal time to mitigate postprandial hyperglycemia. To effectively mitigate postprandial hyperglycemia while also avoiding postprandial hypoglycemia, the user is often required to estimate the amount of carbohydrates being consumed, with that amount of carbohydrates then being utilized to determine the appropriate bolus dosage. While undesirably increasing the burden on the patient for managing his or her therapy, manual errors such as miscounting carbohydrates or failing to initiate a bolus in a timely manner can also reduce the therapy effectiveness. Accordingly, there is a need facilitate improved glucose control that reduces the likelihood of manual errors while also reducing patient workload.

BRIEF SUMMARY

An embodiment of a method of operating an infusion device capable of delivering insulin to a patient is provided. The method involves obtaining, by a control system associated with the infusion device, an input meal indication, obtaining historical data for the patient associated with the input meal indication, determining an estimated carbohydrate amount corresponding to the input meal indication based at least in part on the historical data, determining, by the control system, a bolus dosage of the insulin based at least in part on the estimated carbohydrate amount, and operating, by the control system, an actuation arrangement of the infusion device to deliver the bolus dosage of the insulin to the patient.

In another embodiment, a method of operating an infusion device capable of delivering fluid influencing a physiological condition to a patient involves obtaining, by a control system associated with the infusion device, an indication of an event via a user interface, obtaining historical data for the patient associated with previous instances of the event, determining, by the control system, a delivery adjustment based at least in part on the historical data for the patient associated with the previous instances of the event, and operating, by the control system, an actuation arrangement of the infusion device to deliver the fluid to the patient in accordance with the delivery adjustment.

In yet another embodiment, an infusion system is provided. The infusion system includes an actuation arrangement operable to deliver insulin to a patient, a user interface to receive an input qualitative meal indication, a data storage element to maintain historical meal data for the patient, and a control system coupled to the actuation arrangement, the user interface, and the data storage element. The control system is configurable to determine a meal bolus dosage of the insulin based at least in part on a subset of the historical meal data for the patient corresponding to previous meals corresponding to the input qualitative meal indication and operate the actuation arrangement to deliver the meal bolus dosage of the insulin to the patient.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
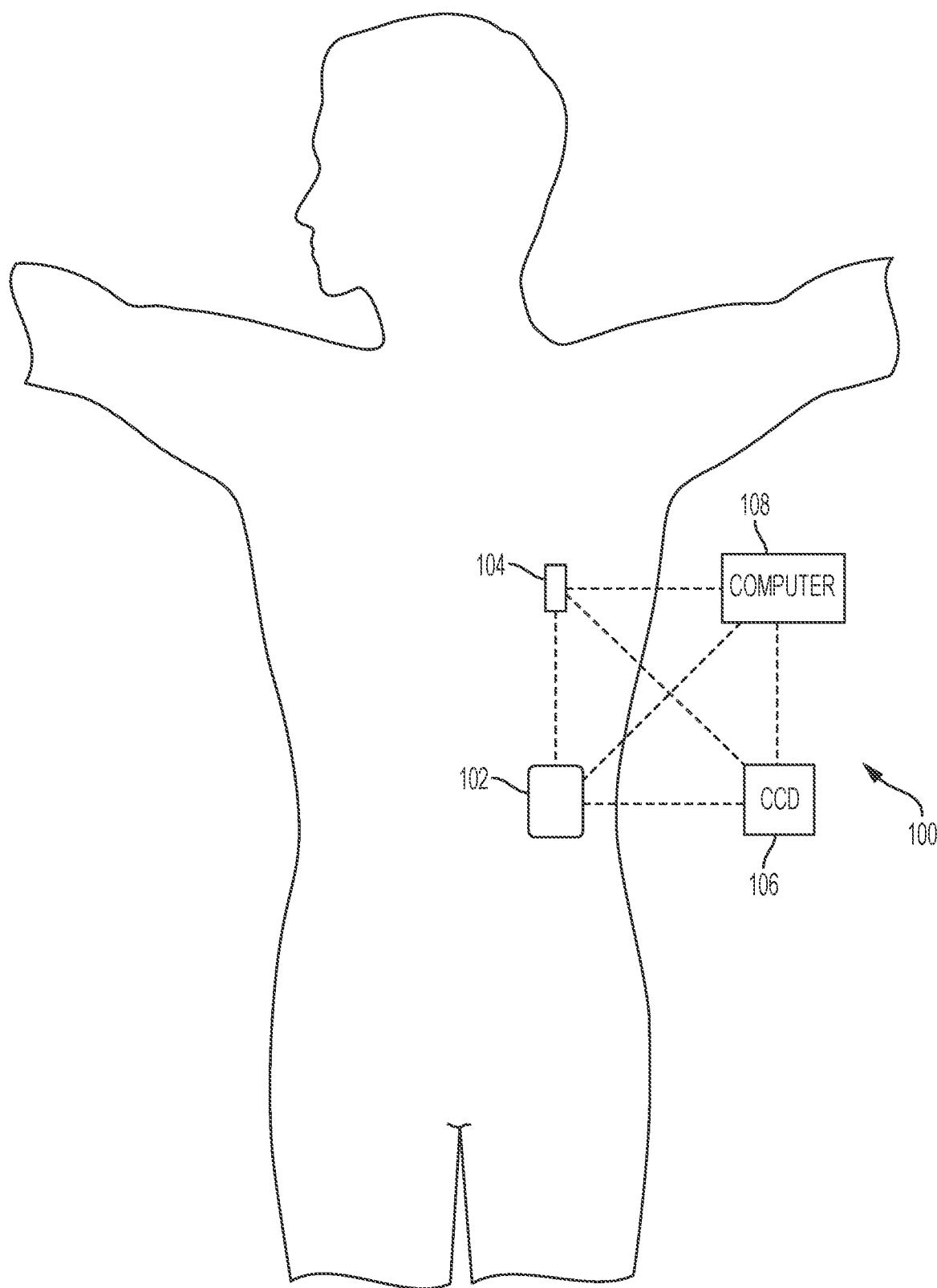
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor or other actuation arrangement that is operable to linearly displace a plunger (or stopper) of a reservoir provided within the fluid infusion device to deliver a dosage of fluid, such as insulin, to the body of a user. In one or more exemplary embodiments, delivery commands (or dosage commands) that govern operation of the motor are determined based on a difference between a measured value for a physiological condition in the body of the user and a target value using closed-loop control to regulate the measured value to the target value. As described in greater detail below, in one or more embodiments, a meal, exercise, or other activity or event that is likely to influence the user's response (or sensitivity) to the fluid being administered is detected or otherwise identified, and at least some of the control information utilized by the closed-loop control to generate delivery commands and operate the infusion device is automatically adjusted to account for the anticipated change in the user's response to the fluid.

For purposes of explanation, the subject matter may be described herein primarily in the context of identifying or detecting a meal for purposes of regulating a glucose level in the body of the user by administering dosages of insulin that account for the meal in a personalized manner. That said, the subject matter described herein is not necessarily limited to glucose regulation, insulin infusion, or meals, and in practice, could be implemented in an equivalent manner with respect to other medications, physiological conditions, exercise or other activities, and/or the like.

As described in greater detail below in the context of FIG. 9, in one or more embodiments, closed-loop control information is adjusted in advance of an anticipated meal, activity, or other event likely to influence the user's glucose levels or insulin response. In this regard, prospective closed-loop control parameter adjustments account for the relatively slow action of long-acting subcutaneously administered insulin by adjusting insulin delivery in advance of a meal in a manner that mitigates postprandial hyperglycemia. Based on historical meal data associated with the user, the likelihood of a future meal event within a specific time period in advance of the current time can be probabilistically determined. The probability of a future meal event could be based on all past meal events for the user or based on a subset of historical meal events corresponding to the current context (e.g., historical meals from weekdays only, historical meals on weekends only, historical meals on the specific day of the week, time of the day, meal content, and/or the like). If the probability of a future meal event within the forecast time period in advance of the current time (e.g., within the next two hours) is greater than a threshold percentage, one or more closed-loop control parameters are automatically adjusted in a manner that is likely to reduce the user's glucose level (or increase yet to be metabolized insulin on board) prior to start of meal consumption. For example, the reference or target glucose value utilized by the closed-loop control algorithm may be reduced to increase insulin delivery. By prospectively adjusting the closed-loop controls in anticipation of a meal, the user may not necessarily be required to proactively and manually deliver a meal bolus or perform other preparatory actions in advance of the meal.

As described in greater detail below in the context of FIG. 10, in one or more embodiments, historical data associated with the user (e.g., historical measurement data, meal data, exercise data, and the like) is analyzed to identify behavior patterns that exhibit a corresponding physiological response. The user's likely engagement in a particular event or activity that is likely to influence the user's glucose level or insulin response is automatically detected based on the correlation between the user's current or recent measurement data and event pattern exhibited by the historical measurement data associated with that particular event or activity. In response to detecting an event pattern in the user's current or recent measurement data, a user notification indicative of the detected event may be automatically generated. In this regard, the user notification may indicate the type of event detected, and potentially other characteristics associated with the event. For example, in the case of a meal event, the user notification may indicate the detected event is a meal and include a detected meal size and/or meal type associated with the detected event pattern. In response to receiving confirmation of the detected event, one or more aspects of operation of the infusion device are automatically adjusted to deliver insulin to the user in a manner that is influenced by the event type and other characteristics associated with the event.

For example, historical data associated with the user may be utilized to correlate sensor glucose measurement patterns for that particular user to a particular size and/or type of meal consumed by the user. In response to detecting a subset of the user's recent measurement data corresponds to the historical measurement data pattern associated with a particular size and type of meal, a user notification may be automatically generated that prompts the user to confirm that he or she has or is consuming that particular size and type of meal. In some embodiments, in response to receiving user confirmation, a meal bolus may be automatically determined based on the confirmed meal size and meal type without requiring any carbohydrate counting or other action by the user.

As described in greater detail below in the context of FIGS. 11-12, in one or more exemplary embodiments, meal bolus dosages are calculated or otherwise determined in a personalized, patient-specific manner. Rather than counting carbohydrates or otherwise quantifying a meal size, the user can input a qualitative meal size, such as small, medium, large, and the like. Based on the user's historical meal data and historical glucose measurement data associated with a particular meal size, a patient-specific carbohydrate ratio associated with that meal size can be determined that accounts for variability in the user's physiological response to meals having that associated size. For example, the rate of glucose appearance after a meal can be influenced by multiple factors, such as the time of day of meal consumption, the particular day of the week, and the order of consumption of meal components for nonhomogeneous meals (e.g., meat before vegetables or vice versa).

In one or more embodiments, historical meal data and contemporaneous historical measurement data are analyzed to mathematically model and optimize the patient-specific carbohydrate ratio for a particular meal size based on that particular patient's postprandial pharmacodynamics following meals of that particular size. In this regard, the optimization may be configured to account for observed diversity in the meal related glucose rate of appearance while also modeling safety and effectiveness of the carbohydrate ratio when utilized for closed-loop control. Based on the patient's historical meal data, an estimated patient-specific carbohydrate amount corresponding to an input meal size may also be determined based on the user's historical meal behavior. Then, in response to an input meal size, the patient-specific estimated carbohydrate amount for that input meal size and the patient-specific carbohydrate ratio associated with that input meal size may be utilized to determine a meal bolus dosage amount in a personalized manner without any carbohydrate counting.

In one or more embodiments, the personalized meal bolus dosage amount or control information associated with the closed-loop operating mode may be further adjusted or modified to account for the particular nutritional content of the meal (or meal type) being consumed. To facilitate meal type adjustments and reduce the user burden, a personalized meal library is created for an individual user based on his or her meal history, and recommended or suggested meals can be prioritized based on correlations to current contextual information (e.g., time of day, day of week, geographic location, etc.). Once sufficient historical meal data for a user exists, a personalized library of likely meal content can be created, with machine learning being utilized to predict the most likely meal content and serving sizes for a meal at the current time (or an anticipated meal in the future) based on the user's historical meal data and the current contextual situation (e.g., the current time of day, current day of week, current geographic location, etc.). A user notification may be provided that includes or otherwise indicates the predicted meal content and size to the user (or an ordered listing of the most likely combinations of meal content and sizes), thereby allowing the user to quickly and conveniently confirm the meal content and size, and without any carbohydrate counting or browsing a list or library of meals when the prediction is correct. Based on the validation or modification of the predicted meal content, the user's historical meal data or prediction model can be dynamically updated in a manner that allows for the accuracy of the predicted meal content to improve over time.

Once the meal content is identified, the bolus dosage amount, bolus dosage schedule, or closed-loop control information may be modified or adjusted to account for the nutritional characteristics of the meal. For example, for a meal earlier in the day including relatively fast acting carbohydrates (e.g., a high carbohydrate breakfast), the bolus dosage amount may be increased (e.g., by scaling the carbohydrate amount by a value greater than one) while also automatically modifying the closed-loop control settings to suspend insulin delivery for at least a minimum suspension threshold amount of time. Conversely, for a relatively high fat meal late in the day (e.g., a high fat dinner), the bolus dosage amount may be decreased while also modifying the closed-loop control settings to increase insulin delivery for a postprandial time period (e.g., by temporarily decreasing the glucose target for the closed-loop control).

As described in greater detail below in the context of FIG. 13, in one or more exemplary embodiments, the bolus dosage amount, bolus dosage schedule, or closed-loop control information may also be modified or adjusted to account for contemporaneous or future activity by the patient. For example, upon the user confirming a meal, administering a meal bolus, or the like, the user may be prompted to provide input pertaining to the user's current or likely activity in the future. In this regard, the user may provide input confirming or indicating whether he or she is or will likely be engaging in exercise, sleep, work, or other activities that may influence the user's glycemic response. Based on the input activity, the bolus dosage or closed-loop controls may be adjusted to account for the user's predicted physiological response to the input activity based on the user's historical physiological response to that particular type of activity using the user's historical sensor glucose measurement data.

Additional contextual information (e.g., time of day, day of week, geographic location, and the like) may also be incorporated to further refine the user's predicted physiological response. Bolus dosages or closed-loop control parameters may then be adjusted to account for the activities that the user is or is likely to be engaged in.

Infusion System Overview

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
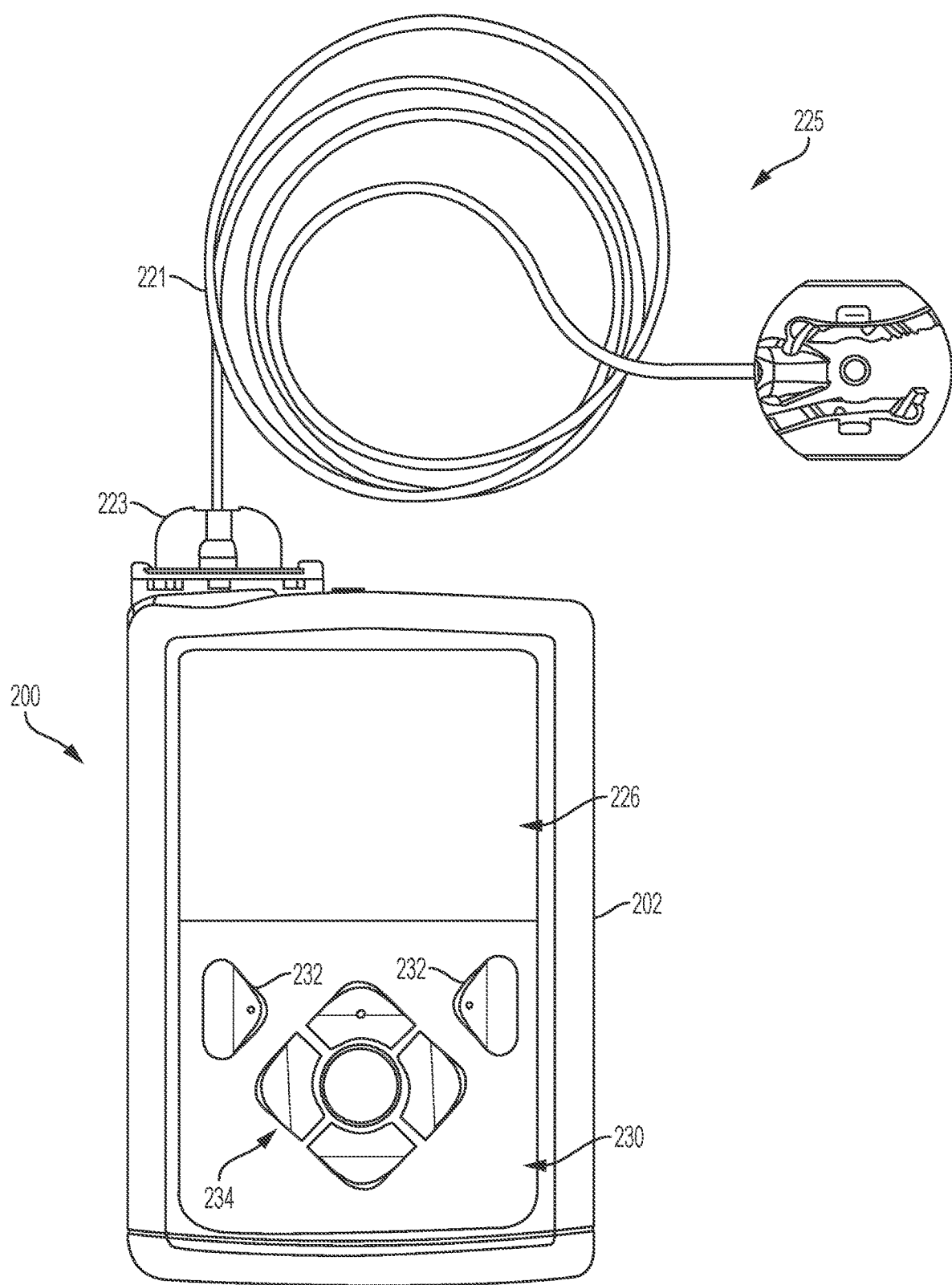
FIG. 2 depicts a plan view of an exemplary embodiment of a fluid infusion device suitable for use in the infusion system of FIG. 1.
Figure 3:
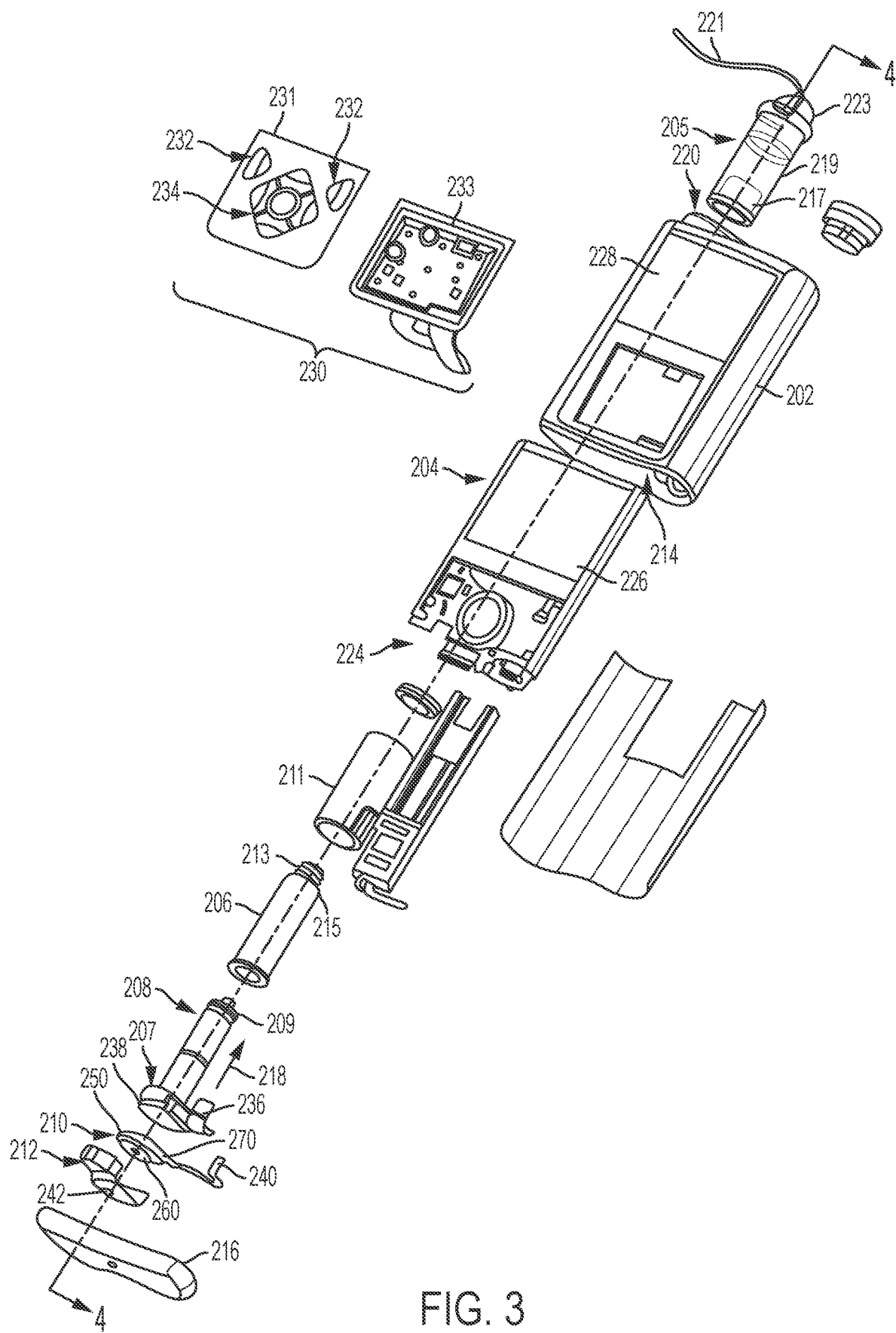
FIG. 3 is an exploded perspective view of the fluid infusion device of FIG. 2.
Figure 4:
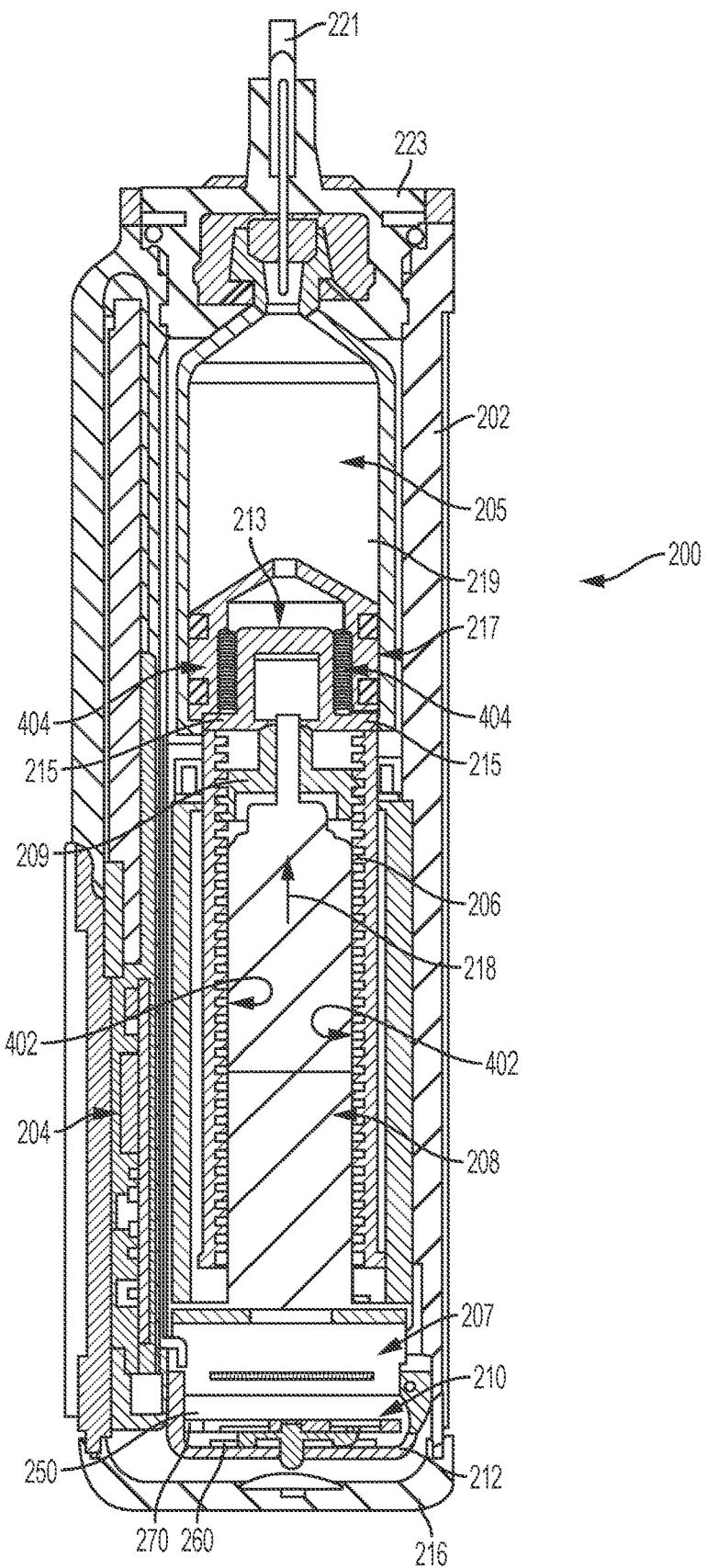
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
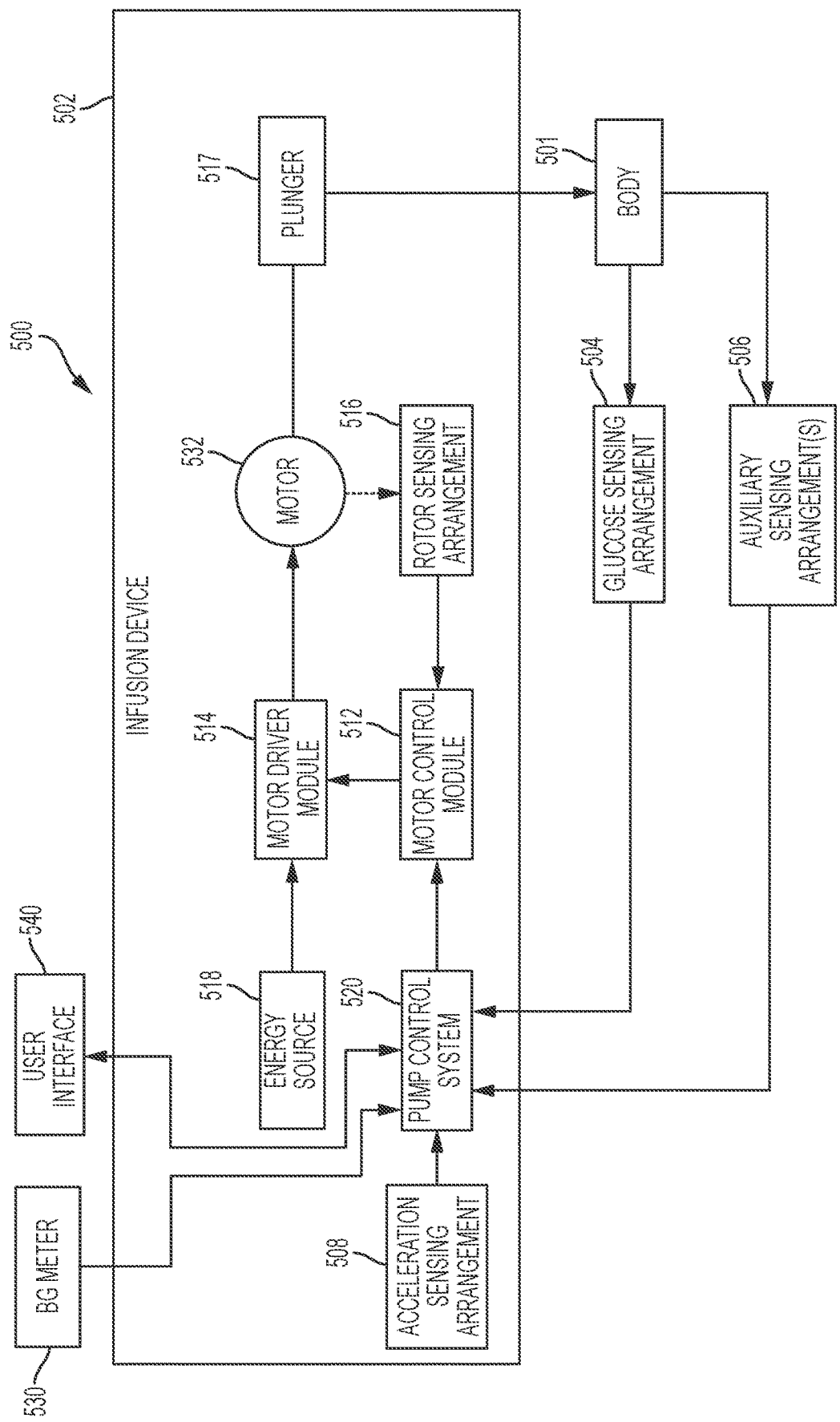
FIG. 5 is a block diagram of an exemplary infusion system suitable for use with a fluid infusion device in one or more embodiments.

FIG. 5 depicts an exemplary embodiment of an infusion system 500 suitable for use with an infusion device 502, such as any one of the infusion devices 102, 200 described above. The infusion system 500 is capable of controlling or otherwise regulating a physiological condition in the body 501 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., sensing arrangement 504) communicatively coupled to the infusion device 502. However, it should be noted that in alternative embodiments, the condition being regulated by the infusion system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the infusion system 500.

In exemplary embodiments, the sensing arrangement 504 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In exemplary embodiments, the infusion system 500 also includes one or more additional sensing arrangements 506, 508 configured to sense, detect, measure or otherwise quantify a characteristic of the body 501 of the user that is indicative of a condition in the body 501 of the user. In this regard, in addition to the glucose sensing arrangement 504, one or more auxiliary sensing arrangements 506 may be worn, carried, or otherwise associated with the body 501 of the user to measure characteristics or conditions of the user (or the user's activity) that may influence the user's glucose levels or insulin sensitivity. For example, a heart rate sensing arrangement 506 could be worn on or otherwise associated with the user's body 501 to sense, detect, measure or otherwise quantify the user's heart rate, which, in turn, may be indicative of exercise (and the intensity thereof) that is likely to influence the user's glucose levels or insulin response in the body 501. In yet another embodiment, another invasive, interstitial, or subcutaneous sensing arrangement 506 may be inserted into the body 501 of the user to obtain measurements of another physiological condition that may be indicative of exercise (and the intensity thereof), such as, for example, a lactate sensor, a ketone sensor, or the like. Depending on the embodiment, the auxiliary sensing arrangement(s) 506 could be realized as a standalone component worn by the user, or alternatively, the auxiliary sensing arrangement(s) 506 may be integrated with the infusion device 502 or the glucose sensing arrangement 504.

The illustrated infusion system 500 also includes an acceleration sensing arrangement 508 (or accelerometer) that may be worn on or otherwise associated with the user's body 501 to sense, detect, measure or otherwise quantify an acceleration of the user's body 501, which, in turn, may be indicative of exercise or some other condition in the body 501 that is likely to influence the user's insulin response. While the acceleration sensing arrangement 508 is depicted as being integrated into the infusion device 502 in FIG. 5, in alternative embodiments, the acceleration sensing arrangement 508 may be integrated with another sensing arrangement 504, 506 on the body 501 of the user, or the acceleration sensing arrangement 508 may be realized as a separate standalone component that is worn by the user.

In the illustrated embodiment, the pump control system 520 generally represents the electronics and other components of the infusion device 502 that control operation of the fluid infusion device 502 according to a desired infusion delivery program in a manner that is influenced by the sensed glucose value indicating the current glucose level in the body 501 of the user. For example, to support a closed-loop operating mode, the pump control system 520 maintains, receives, or otherwise obtains a target or commanded glucose value, and automatically generates or otherwise determines dosage commands for operating an actuation arrangement, such as a motor 532, to displace the plunger 517 and deliver insulin to the body 501 of the user based on the difference between the sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), insulin delivery limit(s), and/or other glucose threshold value(s) in a data storage element accessible to the pump control system 520. As described in greater detail, in one or more exemplary embodiments, the pump control system 520 automatically adjusts or adapts one or more parameters or other control information used to generate commands for operating the motor 532 in a manner that accounts for a likely change in the user's glucose level or insulin response resulting from a meal, exercise, or other activity.

Still referring to FIG. 5, the target glucose value and other threshold glucose values utilized by the pump control system 520 may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 532 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid, such as insulin, that is capable of influencing the user's physiological condition to the body 501 of the user via a fluid delivery path (e.g., via tubing 221 of an infusion set 225). A motor driver module 514 is coupled between an energy source 518 and the motor 532. The motor control module 512 is coupled to the motor driver module 514, and the motor control module 512 generates or otherwise provides command signals that operate the motor driver module 514 to provide current (or power) from the energy source 518 to the motor 532 to displace the plunger 517 in response to receiving, from a pump control system 520, a dosage command indicative of the desired amount of fluid to be delivered.

In exemplary embodiments, the energy source 518 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 518 into alternating electrical signals applied to respective phases of the stator windings of the motor 532 that result in current flowing through the stator windings that generates a stator magnetic field and causes the rotor of the motor 532 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 532 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 532 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 532 to achieve the desired delivery of fluid to the user.

When the motor control module 512 is operating the motor driver module 514, current flows from the energy source 518 through the stator windings of the motor 532 to produce a stator magnetic field that interacts with the rotor magnetic field. In some embodiments, after the motor control module 512 operates the motor driver module 514 and/or motor 532 to achieve the commanded dosage, the motor control module 512 ceases operating the motor driver module 514 and/or motor 532 until a subsequent dosage command is received. In this regard, the motor driver module 514 and the motor 532 enter an idle state during which the motor driver module 514 effectively disconnects or isolates the stator windings of the motor 532 from the energy source 518. In other words, current does not flow from the energy source 518 through the stator windings of the motor 532 when the motor 532 is idle, and thus, the motor 532 does not consume power from the energy source 518 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 502, while in alternative embodiments, the pump control system 520 may be implemented by a remote computing device that is physically distinct and/or separate from the infusion device 502, such as, for example, the CCD 106 or the computing device 108.

Figure 6:
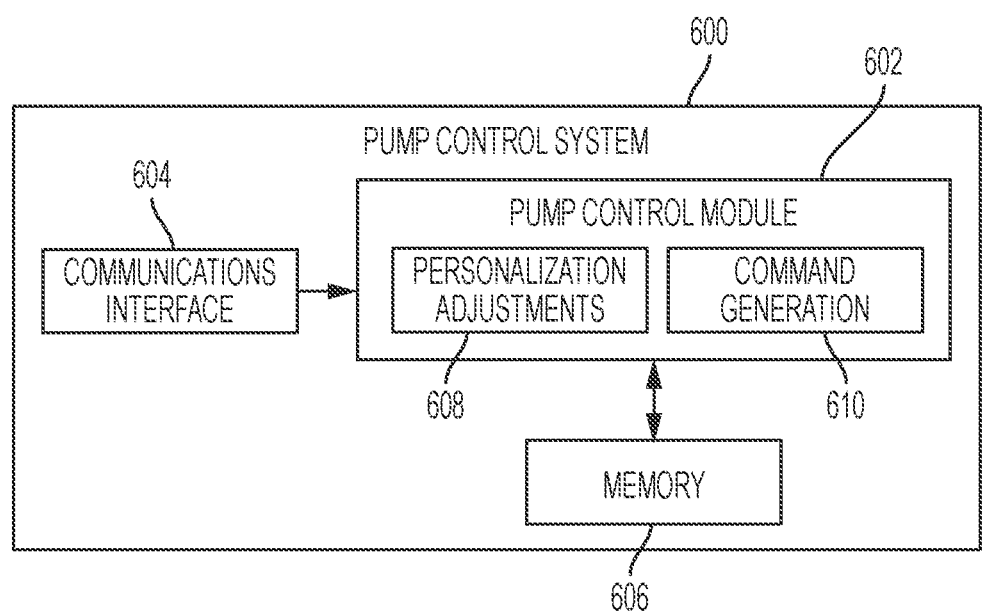
FIG. 6 is a block diagram of an exemplary pump control system suitable for use in the infusion device in the infusion system of FIG. 5 in one or more embodiments.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In various embodiments, the pump control module 602 is also coupled to one or more user interface elements (e.g., user interface 230, 540) for receiving user inputs (e.g., target glucose values or other glucose thresholds) and providing notifications, alerts, or other therapy information to the user.

The communications interface 604 generally represents the hardware, circuitry, logic, firmware and/or other components of the pump control system 600 that are coupled to the pump control module 602 and configured to support communications between the pump control system 600 and the various sensing arrangements 504, 506, 508. In this regard, the communications interface 604 may include or otherwise be coupled to one or more transceiver modules capable of supporting wireless communications between the pump control system 520, 600 and the sensing arrangement 504, 506, 508. For example, the communications interface 604 may be utilized to receive sensor measurement values or other measurement data from each sensing arrangement 504, 506, 508 in an infusion system 500. In other embodiments, the communications interface 604 may be configured to support wired communications to/from the sensing arrangement(s) 504, 506, 508. In various embodiments, the communications interface 604 may also support communications with another electronic device (e.g., CCD 106 and/or computer 108) in an infusion system (e.g., to upload sensor measurement values to a server or other computing device, receive control information from a server or other computing device, and the like).

The pump control module 602 generally represents the hardware, circuitry, logic, firmware and/or other component of the pump control system 600 that is coupled to the communications interface 604 and configured to determine dosage commands for operating the motor 532 to deliver fluid to the body 501 based on measurement data received from the sensing arrangements 504, 506, 508 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 532 of the infusion device 502 in an autonomous operating mode based at least in part on a current measurement value for a condition in the body 501 of the user. For example, in a closed-loop operating mode, the command generation application 610 may determine a dosage command for operating the motor 532 to deliver insulin to the body 501 of the user based at least in part on the current glucose measurement value most recently received from the sensing arrangement 504 to regulate the user's blood glucose level to a target reference glucose value. Additionally, the command generation application 610 may generate dosage commands for boluses that are manually-initiated or otherwise instructed by a user via a user interface element.

In exemplary embodiments, the pump control module 602 also implements or otherwise executes a personalization application 608 that is cooperatively configured to interact with the command generation application 610 to support adjusting dosage commands or control information dictating the manner in which dosage commands are generated in a personalized, user-specific (or patient-specific) manner, as described in greater detail below. In this regard, in some embodiments, based on correlations between current or recent measurement data and the current operational context relative to historical data associated with the patient, the personalization application 608 may adjust or otherwise modify values for one or more parameters utilized by the command generation application 610 when determining dosage commands, for example, by modifying a parameter value at a register or location in memory 606 referenced by the command generation application 610. In yet other embodiments, the personalization application 608 may predict meals or other events or activities that are likely to be engaged in by the user and output or otherwise provide an indication of the predicted user behavior for confirmation or modification by the user, which, in turn, may then be utilized to adjust the manner in which dosage commands are generated to regulate glucose in a manner that accounts for the user's behavior in a personalized manner.

Still referring to FIG. 6, depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the applications 608, 610 and perform tasks, operations, functions, and processes described herein.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
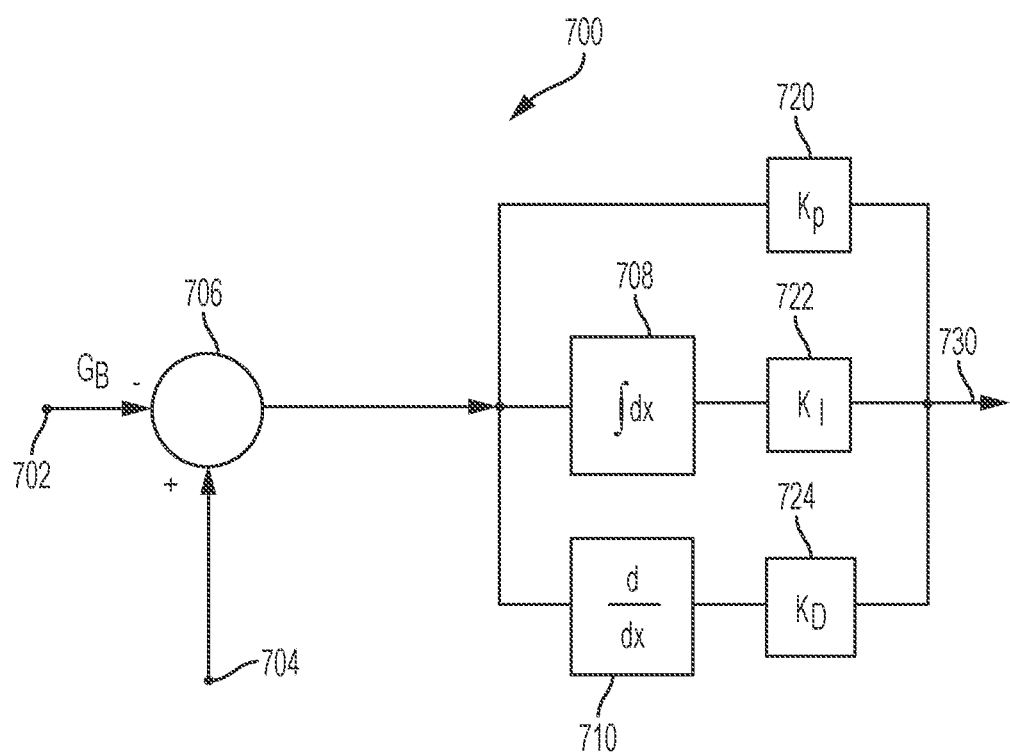
FIG. 7 is a block diagram of a closed-loop control system that may be implemented or otherwise supported by the pump control system in the fluid infusion device of FIGS. 5-6 in one or more exemplary embodiments.

FIG. 7 depicts an exemplary closed-loop control system 700 that may be implemented by a pump control system 520, 600 to provide a closed-loop operating mode that autonomously regulates a condition in the body of a user to a reference (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 510 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 510 to deliver insulin to the body of the user to influence the user's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determining gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

As described in greater detail below, in one or more exemplary embodiments, one or more parameters of the closed-loop control system 700 are automatically adjusted or adapted in a personalized manner to account for potential changes in the user's glucose level or insulin sensitivity resulting from meals, exercise, or other events or activities. For example, in one or more embodiments, the target glucose value 702 may be decreased in advance of a predicted meal event to achieve an increase in the insulin infusion rate to effectively pre-bolus a meal, and thereby reduce the likelihood of postprandial hyperglycemia. Additionally or alternatively, the time constant or gain coefficient associated with one or more paths of the closed-loop control system 700 may be adjusted to tune the responsiveness to deviations between the measured glucose value 704 and the target glucose value 702. For example, based on the particular type of meal being consumed or the particular time of day during which the meal is consumed, the time constant associated with the derivative block 710 or derivative term path may be adjusted to make the closed-loop control more or less aggressive in response to an increase in the user's glucose level based on the user's historical glycemic response to the particular type of meal.

Figure 8:
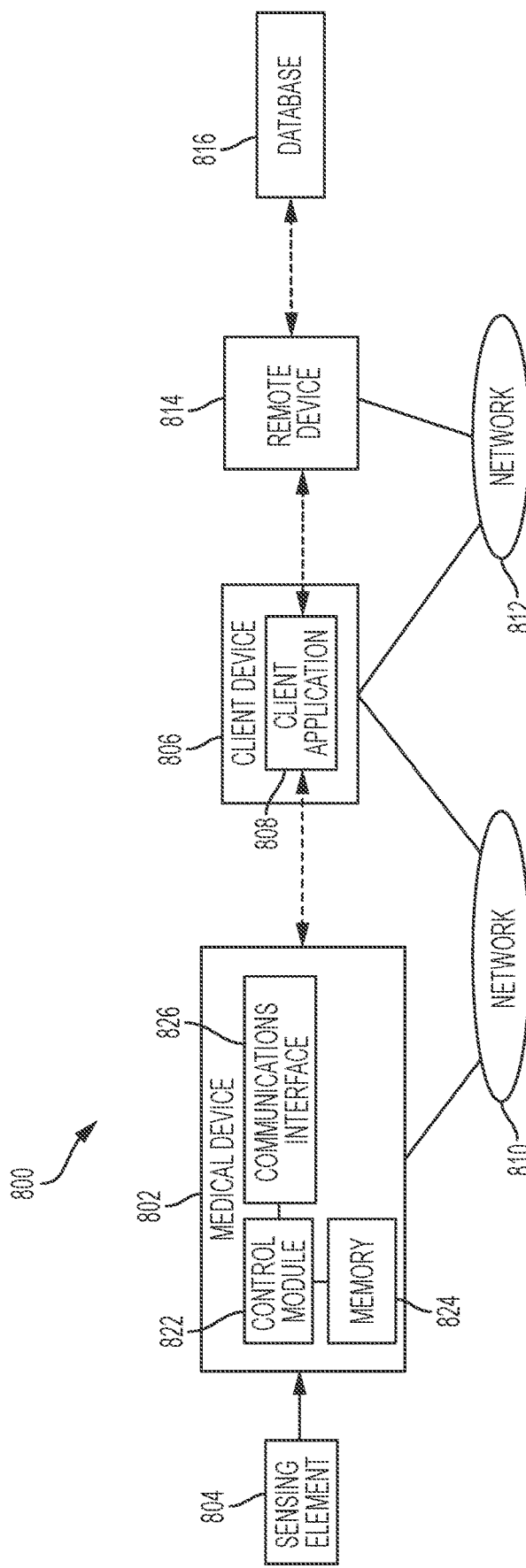
FIG. 8 is a block diagram of an exemplary patient monitoring system.

FIG. 8 depicts an exemplary embodiment of a patient monitoring system 800. The patient monitoring system 800 includes a medical device 802 that is communicatively coupled to a sensing element 804 that is inserted into the body of a patient or otherwise worn by the patient to obtain measurement data indicative of a physiological condition in the body of the patient, such as a sensed glucose level. The medical device 802 is communicatively coupled to a client device 806 via a communications network 810, with the client device 806 being communicatively coupled to a remote device 814 via another communications network 812. In this regard, the client device 806 may function as an intermediary for uploading or otherwise providing measurement data from the medical device 802 to the remote device 814. It should be appreciated that FIG. 8 depicts a simplified representation of a patient monitoring system 800 for purposes of explanation and is not intended to limit the subject matter described herein in any way.

In exemplary embodiments, the client device 806 is realized as a mobile phone, a smartphone, a tablet computer, or other similar mobile electronic device; however, in other embodiments, the client device 806 may be realized as any sort of electronic device capable of communicating with the medical device 802 via network 810, such as a laptop or notebook computer, a desktop computer, or the like. In exemplary embodiments, the network 810 is realized as a Bluetooth network, a ZigBee network, or another suitable personal area network. That said, in other embodiments, the network 810 could be realized as a wireless ad hoc network, a wireless local area network (WLAN), or local area network (LAN). The client device 806 includes or is coupled to a display device, such as a monitor, screen, or another conventional electronic display, capable of graphically presenting data and/or information pertaining to the physiological condition of the patient. The client device 806 also includes or is otherwise associated with a user input device, such as a keyboard, a mouse, a touchscreen, or the like, capable of receiving input data and/or other information from the user of the client device 806.

In exemplary embodiments, a user, such as the patient, the patient's doctor or another healthcare provider, or the like, manipulates the client device 806 to execute a client application 808 that supports communicating with the medical device 802 via the network 810. In this regard, the client application 808 supports establishing a communications session with the medical device 802 on the network 810 and receiving data and/or information from the medical device 802 via the communications session. The medical device 802 may similarly execute or otherwise implement a corresponding application or process that supports establishing the communications session with the client application 808. The client application 808 generally represents a software module or another feature that is generated or otherwise implemented by the client device 806 to support the processes described herein. Accordingly, the client device 806 generally includes a processing system and a data storage element (or memory) capable of storing programming instructions for execution by the processing system, that, when read and executed, cause processing system to create, generate, or otherwise facilitate the client application 808 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random access memory (RAM), read only memory (ROM), flash memory, magnetic or optical mass storage, or any other suitable non-transitory short or long term data storage or other computer-readable media, and/or any suitable combination thereof.

In one or more embodiments, the client device 806 and the medical device 802 establish an association (or pairing) with one another over the network 810 to support subsequently establishing a point-to-point or peer-to-peer communications session between the medical device 802 and the client device 806 via the network 810. For example, in accordance with one embodiment, the network 810 is realized as a Bluetooth network, wherein the medical device 802 and the client device 806 are paired with one another (e.g., by obtaining and storing network identification information for one another) by performing a discovery procedure or another suitable pairing procedure. The pairing information obtained during the discovery procedure allows either of the medical device 802 or the client device 806 to initiate the establishment of a secure communications session via the network 810.

In one or more exemplary embodiments, the client application 808 is also configured to store or otherwise maintain an address and/or other identification information for the remote device 814 on the second network 812. In this regard, the second network 812 may be physically and/or logically distinct from the network 810, such as, for example, the Internet, a cellular network, a wide area network (WAN), or the like. The remote device 814 generally represents a server or other computing device configured to receive and analyze or otherwise monitor measurement data, event log data, and potentially other information obtained for the patient associated with the medical device 802. In exemplary embodiments, the remote device 814 is coupled to a database 816 configured to store or otherwise maintain data associated with individual patients. In practice, the remote device 814 may reside at a location that is physically distinct and/or separate from the medical device 802 and the client device 806, such as, for example, at a facility that is owned and/or operated by or otherwise affiliated with a manufacturer of the medical device 802. For purposes of explanation, but without limitation, the remote device 814 may alternatively be referred to herein as a server.

Still referring to FIG. 8, the sensing element 804 generally represents the component of the patient monitoring system 800 that is configured to generate, produce, or otherwise output one or more electrical signals indicative of a physiological condition that is sensed, measured, or otherwise quantified by the sensing element 804. In this regard, the physiological condition of a user influences a characteristic of the electrical signal output by the sensing element 804, such that the characteristic of the output signal corresponds to or is otherwise correlative to the physiological condition that the sensing element 804 is sensitive to. In exemplary embodiments, the sensing element 804 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 804.

The medical device 802 generally represents the component of the patient monitoring system 800 that is communicatively coupled to the output of the sensing element 804 to receive or otherwise obtain the measurement data samples from the sensing element 804 (e.g., the measured glucose and characteristic impedance values), store or otherwise maintain the measurement data samples, and upload or otherwise transmit the measurement data to the server 814 via the client device 806. In one or more embodiments, the medical device 802 is realized as an infusion device 102, 200, 502 configured to deliver a fluid, such as insulin, to the body of the patient. That said, in other embodiments, the medical device 802 could be a standalone sensing or monitoring device separate and independent from an infusion device (e.g., sensing arrangement 104, 504). It should be noted that although FIG. 8 depicts the medical device 802 and the sensing element 804 as separate components, in practice, the medical device 802 and the sensing element 804 may be integrated or otherwise combined to provide a unitary device that can be worn by the patient.

In exemplary embodiments, the medical device 802 includes a control module 822, a data storage element 824 (or memory), and a communications interface 826. The control module 822 generally represents the hardware, circuitry, logic, firmware and/or other component(s) of the medical device 802 that is coupled to the sensing element 804 to receive the electrical signals output by the sensing element 804 and perform or otherwise support various additional tasks, operations, functions and/or processes described herein. Depending on the embodiment, the control module 822 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 822 includes an analog-to-digital converter (ADC) or another similar sampling arrangement that samples or otherwise converts an output electrical signal received from the sensing element 804 into corresponding digital measurement data value. In other embodiments, the sensing element 804 may incorporate an ADC and output a digital measurement value.

The communications interface 826 generally represents the hardware, circuitry, logic, firmware and/or other components of the medical device 802 that are coupled to the control module 822 for outputting data and/or information from/to the medical device 802 to/from the client device 806. For example, the communications interface 826 may include or otherwise be coupled to one or more transceiver modules capable of supporting wireless communications between the medical device 802 and the client device 806. In exemplary embodiments, the communications interface 826 is realized as a Bluetooth transceiver or adapter configured to support Bluetooth Low Energy (BLE) communications.

In exemplary embodiments, the remote device 814 receives, from the client device 806, measurement data values associated with a particular patient (e.g., sensor glucose measurements, acceleration measurements, and the like) that were obtained using the sensing element 804, and the remote device 814 stores or otherwise maintains the historical measurement data in the database 816 in association with the patient (e.g., using one or more unique patient identifiers). Additionally, the remote device 814 may also receive, from or via the client device 806, meal data or other event log data that may be input or otherwise provided by the patient (e.g., via client application 808) and store or otherwise maintain historical meal data and other historical event or activity data associated with the patient in the database 816. In this regard, the meal data include, for example, a time or timestamp associated with a particular meal event, a meal type or other information indicative of the content or nutritional characteristics of the meal, and an indication of the size associated with the meal. In exemplary embodiments, the remote device 814 also receives historical fluid delivery data corresponding to basal or bolus dosages of fluid delivered to the patient by an infusion device 102, 200, 502. For example, the client application 808 may communicate with an infusion device 102, 200, 502 to obtain insulin delivery dosage amounts and corresponding timestamps from the infusion device 102, 200, 502, and then upload the insulin delivery data to the remote device 814 for storage in association with the particular patient. The remote device 814 may also receive geolocation data and potentially other contextual data associated with a device 802, 806 from the client device 806 and/or client application 808, and store or otherwise maintain the historical operational context data in association with the particular patient. In this regard, one or more of the devices 802, 806 may include a global positioning system (GPS) receiver or similar modules, components or circuitry capable of outputting or otherwise providing data characterizing the geographic location of the respective device 802, 806 in real-time.

The historical patient data may be analyzed by one or more of the remote device 814, the client device 806, and/or the medical device 802 to alter or adjust operation of an infusion device 102, 200, 502 to influence fluid delivery in a personalize manner. For example, the patient's historical meal data and corresponding measurement data or other contextual data may be analyzed to predict a future time when the next meal is likely to be consumed by the patient, the likelihood of a future meal event within a specific time period, the likely size or amount of carbohydrates associated with a future meal, the likely type or nutritional content of the future meal, and/or the like. Moreover, the patient's historical measurement data for postprandial periods following historical meal events may be analyzed to model or otherwise characterize the patient's glycemic response to the predicted size and type of meal for the current context (e.g., time of day, day of week, geolocation, etc.). One or more aspects of the infusion device 102, 200, 502 that control or regulate insulin delivery may then be modified or adjusted to proactively account for the patient's likely meal activity and glycemic response.

In one or more exemplary embodiments, the remote device 814 utilizes machine learning to determine which combination of historical sensor glucose measurement data, historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular event, activity, or metric for a particular patient, and then determines a corresponding equation, function, or model for calculating the value of the parameter of interest based on that set of input variables. Thus, the model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other users. Additionally, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 814 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

Prospective Meal Adjustments

Figure 9:
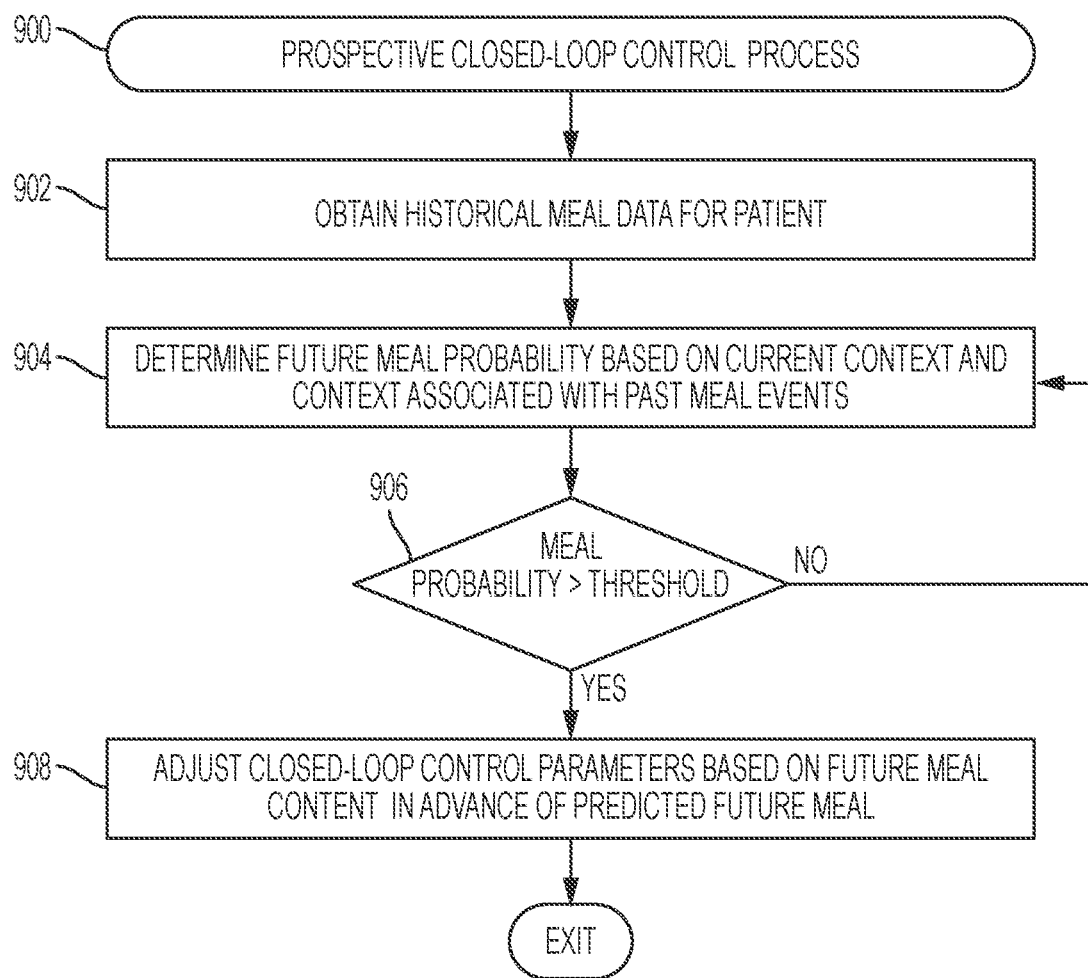
FIG. 9 is a flow diagram of an exemplary prospective closed-loop control process suitable implementation in connection with an infusion device in one or more exemplary embodiments.

FIG. 9 depicts an exemplary prospective closed-loop control process 900 suitable for implementation by an infusion device (or a control system associated therewith) to automatically adjust closed-loop control information in advance of a meal or other future event or activity that is likely to influence a patient's glucose level or insulin response. In this regard, the prospective closed-loop control process 900 compensates for the relatively slow action of subcutaneously infused insulin by proactively adjusting insulin infusion rates to account for the patient's likely glycemic response to the future event.

The various tasks performed in connection with the control process 900 may be performed by hardware, firmware, software executed by processing circuitry, or any combination thereof. For illustrative purposes, the following description refers to elements mentioned above in connection with FIGS. 1-8. In practice, portions of the control process 900 may be performed by different elements of an infusion system, such as, for example, an infusion device 102, 200, 502, 802, a client computing device 106, 806, a remote computing device 108, 814, and/or a pump control system 520, 600. It should be appreciated that the control process 900 may include any number of additional or alternative tasks, the tasks need not be performed in the illustrated order and/or the tasks may be performed concurrently, and/or the control process 900 may be incorporated into a more comprehensive procedure or process having additional functionality not described in detail herein. Moreover, one or more of the tasks shown and described in the context of FIG. 9 could be omitted from a practical embodiment of the control process 900 as long as the intended overall functionality remains intact.

The illustrated prospective closed-loop control process 900 begins by receiving or otherwise obtaining historical meal data for the patient and calculating or otherwise determining a future meal probability based at least in part on the correlation between the current operational context and the historical operational context associated with past meal events (tasks 902, 904). For example, one of an infusion device 102, 200, 502, 802, a client device 106, 806, or a remote computing device 108, 814 may retrieve or otherwise obtain the historical meal data associated with the patient from the database 816 and analyze the historical meal data to identify previous meal events logged, entered, or otherwise input by the patient or other user of the client device 106, 806. Based on the timestamps associated with those previous meal events and potentially other contextual information pertaining to operation of the infusion device 102, 200, 502, 802 (e.g., geolocation data, and/or the like), the probability of the patient consuming a meal at a particular point in time in the future or within a future prediction window (or horizon) in advance of the current time may be calculated based at least in part on the current operational context (e.g., the current time of day, the current day of the week, current geographic location of the infusion device 102, 200, 502, 802 or the client device 106, 806, and the like).

For example, each day (or 24-hour period) may be divided into a number of smaller time segments, with past meal events being assigned to particular individual segments of the day. In one exemplary embodiment, each day is divided into 15 minute segments (or 96 total segments per day). For each 15 minute segment, any meal event timestamped within a prediction horizon (e.g., the next 60 minutes) is assigned to that segment. The probability of meal presence within the prediction horizon can be determined using a conditional probabilistic model by dividing the number of days where there was a meal event within the prediction horizon for the current segment by the total number of days of meal history that exist. For example, if the current segment corresponds to the period between 8:00 A.M. and 8:15 A.M., the prediction horizon is 60 minutes, and for 7 days out of the 10 days of meal history the patient consumed a meal within the period between 8:00 A.M. and 9:00 A.M., the future meal probability may be estimated to be 70% at or within the time period between 8:00 A.M. and 8:15 A.M.

Additionally, for each segment, the probability of a particular size or type of meal being consumed within the prediction horizon may also be determined by dividing the number of meals assigned to a particular size or type by the total number of meals within that prediction horizon. For example, for the 7 meals consumed within the period between 8:00 A.M. and 9:00 A.M., 4 meal events may have been indicated as having a small size, 2 meal events may have been indicated as having a medium or normal size, and 1 meal event may have been indicated as having a large size. Accordingly, the probability of a small meal may be estimated as 57%, the probability of a normal meal may be estimated as 29%, and the probability of a large meal may be estimated as 14%. In a similar manner, where meal events are logged or tagged with a particular type of nutritional content, the prospective closed-loop control process 900 may be configured to probabilistically determine the likely nutritional content for a future meal within the prediction horizon.

It should be noted that the historical meal data utilized to determine the future meal probabilities may be filtered to account for the current day of the week, the current geographic location of the patient, or potentially other factors. For example, continuing the above example, there may be 70 days worth of patient history accounted for by the patient's historical meal data, but with only 10 of those days corresponding to the current day of the week. The historical meal data for those 10 days may then be utilized to determine meal probabilities for the current day of the week as described above.

In one or more exemplary embodiments, the remote device 814 may determine meal probabilities or predicted future meal times for the patient and provide indication of the calculated meal probabilities to the infusion device 802 or the client device 806. However, in alternative embodiments, the personalization application 608 at the infusion device 802 or the client application 808 at the client device 806 may request or retrieve historical meal data for the current context from the database 816 via the remote device 814 and determine meal probabilities or predicted future meal times for the patient substantially in real-time at the respective device 802, 806.

In another embodiment, machine learning is utilized to determine personalized models for meal probability (or probability of meal occurrence) and meal size, which, in turn, may be utilized to calculate meal probability and probable meal size substantially in real-time as a function of current measurement data and other current operational context information. For example, the remote device 814 may analyze the historical meal data, historical sensor glucose measurement data, historical insulin delivery data, historical auxiliary measurement data, historical geographic location data, and any other historical data associated with the patient in the database 816 to identify or otherwise determine the subset of the patient's historical data that is predictive of or correlative to meal occurrence. The remote device 814 may then determine a corresponding equation for calculating a meal probability value based on that subset of input variables, thereby characterizing or mapping a particular combination of values or attributes for the current operational context to a corresponding meal probability. In one or more embodiments, different meal probability models are determined for different times of the day (e.g., for a breakfast period to be utilized between 6 A.M. and 10 A.M., a lunch period to be utilized between 10 A.M. and 2 P.M., and so on), different days of the week (e.g., a weekday model for the breakfast period versus a weekend model for the breakfast period), different geographic locations, or other operational contexts. Similarly, the remote device 814 may analyze the historical meal data, historical sensor glucose measurement data, historical insulin delivery data, historical auxiliary measurement data, historical geographic location data, and any other historical data associated with the patient in the database 816 to identify or otherwise determine the subset of the patient's historical data that is predictive of or correlative to a particular meal size, and then determine a corresponding equation for calculating a probable carbohydrate value based on that subset of input variables. Such machine learning models may be dynamically determined or updated on a periodic basis (e.g., daily, weekly, monthly, or the like) to reflect changes or trends in the patient's behavior. In various embodiments, the remote device 814 automatically pushes updated models to the client application 808 or the personalization application 608, which, in turn utilize the models to continually calculate predicted meal probabilities and corresponding meal sizes substantially in real-time as new sensor glucose measurement data or other auxiliary measurement data is available, as the geographic location of the respective device 802, 806 changes, the time of day changes, and so on.

Still referring to FIG. 9, in response to determining the predicted future meal probability is greater than a threshold, the prospective closed-loop control process 900 automatically adjusts or modifies control information associated with the closed-loop control scheme to proactively increase insulin delivery in anticipation of a future meal in advance of receiving any meal indication from the patient (tasks 906, 908). For example, in one or more embodiments, the pump control system 520, 600 may automatically reduce the target glucose value 702 for a temporary duration of time corresponding to the prediction horizon when the predicted future meal probability within the prediction horizon is greater than a threshold value (e.g., greater than 50%). In some embodiments, the amount by which the target glucose value 702 is reduced is dependent on or influenced by the probable meal size. For example, if the most probable meal size is classified or characterized as a small meal, the target glucose value 702 may be reduced from 120 milligrams per deciliter (mg/dL) to 100 mg/dL, while the target glucose value 702 may be reduced to 85 mg/dL when a normal or medium meal is most probable and to 70 mg/dL when a large meal is most probable. Additionally or alternatively, the pump control system 520, 600 may automatically adjust one or more other control parameters or settings associated with the control scheme, such as, for example, increasing the minimum or maximum basal delivery rates. In one or more embodiments, the pump control system 520, 600 may automatically operate the motor 532 to deliver a correction bolus in advance of receiving any meal indication.

In one or more embodiments, the type or magnitude of the automated adjustments performed by the pump control system 520, 600 are influenced by the future meal probability and/or the probable future meal size or content. For example, when the probable future meal size within the prediction horizon corresponds to a large meal with a relatively high meal probability (e.g., greater than 75% probability of a large meal within the prediction horizon), the pump control system 520, 600 may automatically reduce the target glucose value 702 and increase one or more minimum or maximum basal delivery rate settings while also determining a correction bolus dosage based on the predicted meal size to mitigate the likelihood of a postprandial hyperglycemic excursion. Conversely, for a probable future meal size within the prediction horizon corresponding to a small meal with a relatively lower meal probability (e.g., between 50% and 75% meal probability), the pump control system 520, 600 may automatically reduce the target glucose value 702 without modifying basal delivery rate settings or administering a correction bolus to reduce the likelihood of a hypoglycemic excursion in the event a meal is not consumed.

It should be noted that in some embodiments, the predicted meal size may be determined as a weighted average of the estimated carbohydrate amounts associated with the different meal sizes. For example, continuing the above example, if the small meal size corresponds to 15 grams of carbohydrates, the normal meal size corresponds to 30 grams of carbohydrates, and the large meal size corresponds to 50 grams for the particular patient, the predicted or probable meal size may be determined as a weighted sum of the patient-specific meal sizes with the respective probabilities (e.g., 57%×15+29%×30+14%×50=24.3 carbohydrates). Thus, the amount of adjustment to the closed-loop control information may correspond to the weighted average of the patient-specific meal sizes according to their likely probabilities.

In one or more embodiments, after a period of time has elapsed without receiving a meal indication, the prospective closed-loop control process 900 may automatically revert to the original or normal closed-loop control information. For example, once the prediction horizon duration of time has elapsed since adjusting the target glucose value 702, the pump control system 520, 600 may automatically restore the target glucose value 702 to its original reference value (e.g., 120 mg/dL). In other embodiments, the prospective closed-loop control process 900 is configured to continually analyze the predicted meal probability and maintain the adjusted closed-loop control information until the predicted meal probability for the current segment falls below the threshold for triggering adjustment at 906. For example, every 15 minutes, the prospective closed-loop control process 900 may determine an updated predicted meal probability for the current segment, and maintain the adjusted closed-loop control information until the predicted meal probability falls back below the threshold (e.g., below 50%).

Some embodiments of the prospective closed-loop control process 900 may determine a predicted meal time for a future meal based on the patient's historical meal distribution. For example, when the meal probability based on a number of consecutive or contiguous segments is greater than the threshold, the timestamps associated with individual historical meal events assigned to those relevant segments of the day may be averaged or otherwise analyzed to determine a predicted future meal time. In this regard, the patient's historical meal data may be analyzed to identify a subset of time segments or windows having the highest meal probabilities, which may then be utilized to calculate or otherwise determine predicted times for when the patient is likely to eat breakfast, lunch, or dinner in the future. More recent meal events may be weighted more heavily than older meal events to adaptively adjust the predicted meal times over time as the patient's behavior changes. The prospective closed-loop control process 900 may then automatically adjust or modify control information associated with the closed-loop control scheme based on the predicted future meal time. For example, the pump control system 520, 600 may identify when the current time is within a threshold amount of time in advance of a predicted future meal time (e.g., one hour before a predicted meal time), and then automatically initiate adjustments of the control information at that time. It should be noted that there are numerous different ways to model a patient's meal behavior and predict when a patient is likely to eat a meal with a given amount of accuracy or reliability, and the subject matter describe herein is not necessarily intended to be limited to any particular manner or method for predicting whether or when a patient is likely to consume a future meal.

In one or more embodiments, the closed-loop control system 700 is modified to include an additional input corresponding to the meal probability corresponding to the current instant in time, that is, the probability of a meal event being consumed within the forecast window in advance of the current time. In such embodiments, the future meal probability may be utilized to dynamically adjust the target glucose value 702 as the future meal probability fluctuates (e.g., by calculating an adjusted target value input to the summation block 706 as a function of the target glucose value 702 and the current meal probability).

As yet another example, when personalized machine learning models are utilized the automated control adjustments may be dynamically initiated or terminated in real-time based on real-time changes to measurement data or other inputs to the models. For example, each time a new measurement data sample is received by the infusion device 102, 200, 502, 802 from a sensing device 104, 504, 506, 508, 804, the personalization application 608 may automatically determine an updated meal probability value using the patient-specific meal probability model corresponding to the current time of day for the current day of the week and the current geographic location of the infusion device 102, 200, 502, 802. Once the calculated meal probability value based on the current operational context is greater than an adjustment threshold, the personalization application 608 may automatically initiate adjustment to the closed-loop control system 700 implemented by the command generation application 610. The personalization application 608 may continually and dynamically determine updated meal probability values as new measurement data samples are continued to be received until the updated meal probability value falls below a reversion threshold (which could be the same as or different from the adjustment threshold for hysteresis), at which point the personalization application 608 automatically undoes adjustment to the closed-loop control system 700 to revert to the original or previous configuration.

In some embodiments, the personalization application 608 may dynamically vary the adjustments to the closed-loop control system 700 to reflect real-time fluctuations in the probable meal size. For example, once the meal probability is greater than an adjustment threshold, the personalization application 608 may automatically determine a probable meal size using the patient-specific meal size model corresponding to the current time of day for the current day of the week and the current geographic location of the infusion device 102, 200, 502, 802 and automatically adjust the closed-loop control system 700 according to the probable meal size. Thereafter, the personalization application 608 may dynamically determine updated probable meal sizes as new measurement data samples are continued to be received, and dynamically adjust the closed-loop control system 700 to reflect changes in the probable meal size. For example, as the probable meal size dynamically increases, the personalization application 608 may progressively reduce the target glucose value 702 in a manner commensurate to the probable meal size.

It should be noted that the prospective closed-loop control process 900 may improve postprandial glucose management by effectively pre-bolusing or pre-loading insulin prior to consumption of a meal to overcome the relatively slow action of subcutaneously administered insulin. The patient burden of carbohydrate counting or manually remembering to administer a bolus or increase insulin delivery before a meal, which may be particular advantageous in instances where the patient consumes a meal relatively soon after waking (e.g., breakfast) or engaging in some other activity where manually preparing for a meal is inconvenient or cumbersome.

Event Pattern Control Process

Figure 10:
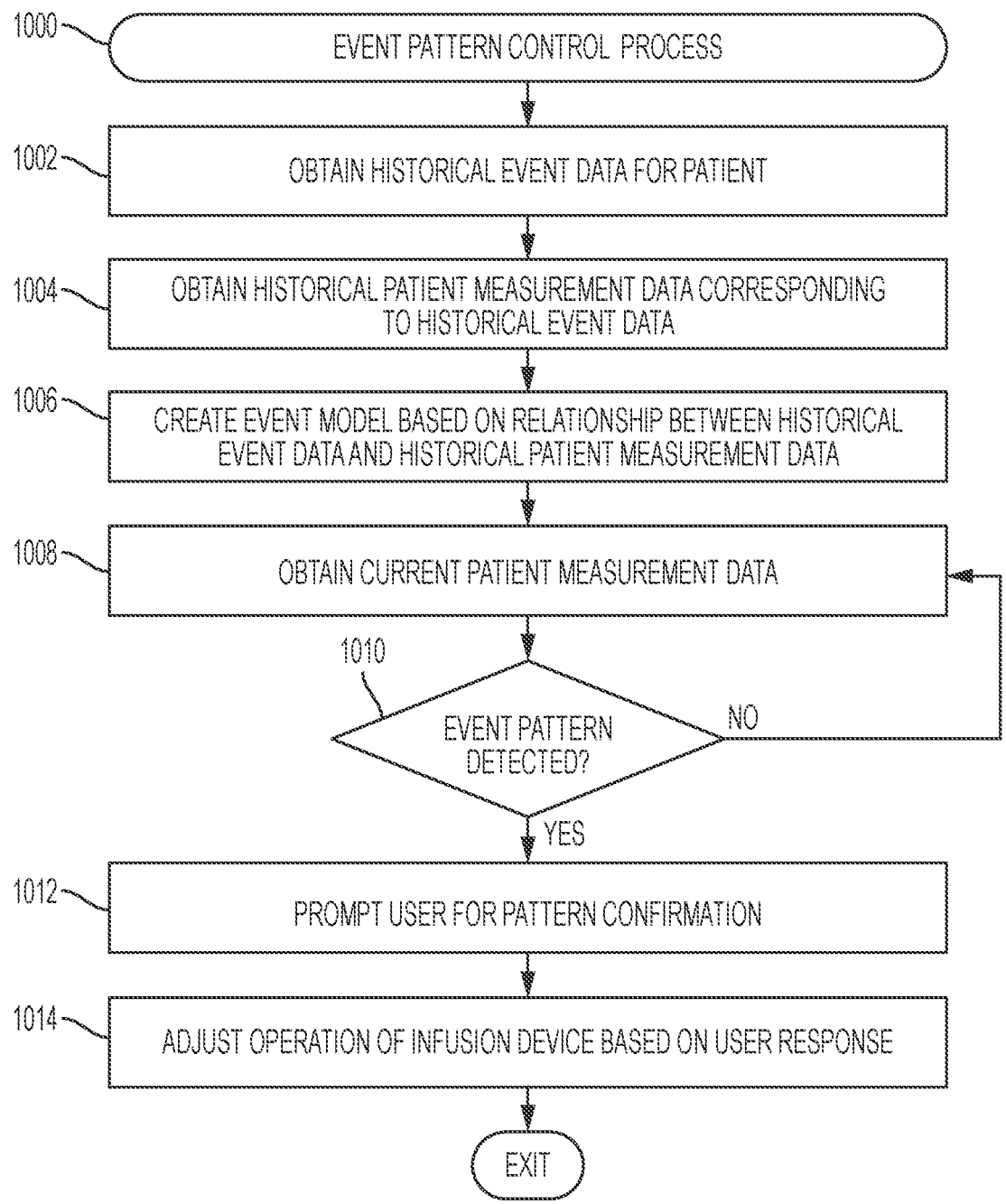
FIG. 10 is a flow diagram of an exemplary event pattern control suitable implementation in connection with an infusion device in one or more exemplary embodiments.

FIG. 10 depicts an exemplary event pattern control process 1000 suitable for implementation by an infusion device (or a control system associated therewith) to automatically detect and respond to an event or activity that is likely to influence an individual's glucose level or insulin response, such as, for example, a meal event, an exercise event, a stress event, or the like. In this regard, the event pattern control process 1000 detects or otherwise identifies the likely occurrence of an event and prompts the patient accordingly, thereby alleviating some of the burden of manually logging the event and manually configuring the infusion device to respond to the event.

The various tasks performed in connection with the control process 1000 may be performed by hardware, firmware, software executed by processing circuitry, or any combination thereof. For illustrative purposes, the following description refers to elements mentioned above in connection with FIGS. 1-8. In practice, portions of the control process 1000 may be performed by different elements of an infusion system, such as, for example, an infusion device 102, 200, 502, 802, a client computing device 106, 806, a remote computing device 108, 814, and/or a pump control system 520, 600. It should be appreciated that the control process 1000 may include any number of additional or alternative tasks, the tasks need not be performed in the illustrated order and/or the tasks may be performed concurrently, and/or the control process 1000 may be incorporated into a more comprehensive procedure or process having additional functionality not described in detail herein. Moreover, one or more of the tasks shown and described in the context of FIG. 10 could be omitted from a practical embodiment of the control process 1000 as long as the intended overall functionality remains intact.

The event pattern control process 1000 initializes or begins by receiving or otherwise obtaining historical event data associated with the patient and historical measurement data associated with the patient that corresponds to the historical event data (tasks 1002, 1004). The illustrated event pattern control process 1000 then creates or otherwise generates a patient-specific model for detecting the event as a function of the patient's measurement data based on the relationship between the historical event data and the corresponding historical measurement data (task 1006). In this regard, for an event to be modeled, one of an infusion device 102, 200, 502, 802, a client device 106, 806, or a remote computing device 108, 814 may retrieve or otherwise obtain the historical data for that event that is associated with the patient from the database 816 and analyze the historical event data to identify previous events logged, entered, or otherwise input by the patient or other user of the client device 106, 806. Based on the timestamps associated with those previous events, the historical measurement data associated with the patient that is concurrent to, contemporaneous to, or surrounding the individual historical events is also obtained from the database 816. In a similar manner as described above, for each historical event to be detected, the patient's historical sensor glucose measurement data and any other historical auxiliary measurement data (e.g., accelerometer data, heart rate measurement data, geolocation data, or the like), historical delivery data, and/or other historical patient data at or around the time of the event is obtained for analyzing the relationship or correlation between the historical event data and the historical patient's measurement data to identify or otherwise determine the subset of the variables that is predictive of or correlative to the occurrence or other attributes of the event to be detected. A corresponding equation, function, or model may then be created for calculating a probability of occurrence or other value or metric for the event based on that correlative subset of input variables to thereby map the operational context to a corresponding probability or attribute of the event.

For example, for each meal event, the patient's sensor glucose measurement data for a preprandial period (e.g., one hour preceding the meal) and a postprandial period (e.g., one hour following the meal) may be selected for analyzing the relationship between the patient's sensor glucose measurement data and the patient consuming a meal. As another example, for each exercise event, the patient's sensor glucose measurement data and accelerometer measurement data for the duration of the exercise event along may be selected for analyzing the relationship between the patient's measurement data and the patient engaging in exercise. Additionally, sensor glucose measurement data preceding or following the exercise event may also be selected for modeling the patient's glycemic response to exercise.

Based on the relationship or correlation between the patient's historical measurement data and the patient's historical event data, the infusion device 102, 200, 502, 802, the client device 106, 806, or the remote computing device 108, 814 may create, develop, or otherwise generate a model for determining the probability or likelihood of the patient experiencing that event as a function of the patient's measurement data. In one or more embodiments, the patient's historical measurement data may be utilized to train a neural network or other artificial intelligence or machine learning model and develop a function for predicting the likelihood of occurrence of a particular event as a function of the patient's measurement data. For example, a model may be developed that predicts the likelihood of a patient having consumed a meal as a function of the patient's sensor glucose measurement data, the patient's heart rate measurement data, the patient's acceleration measurement data, and/or the patient's geolocation data. Similarly, as another example, a model may be developed that predicts the likelihood of a patient having engaged in exercise as a function of the patient's sensor glucose measurement data, the patient's heart rate measurement data, the patient's acceleration measurement data, and/or the patient's geolocation data. In various embodiments, models may be developed to predict attributes of a particular event, such as, for example, meal size, meal content, exercise intensity, and the like.

Still referring to FIG. 10, in exemplary embodiments, the event pattern control process 1000 continues by receiving or otherwise obtaining current measurement data for the patient and detecting or otherwise identifying the occurrence of an event based on the relationship or correlation between the patient's current measurement data and the patient's historical measurement data associated with occurrences of that type of event (tasks 1008, 1010). In this regard, in a similar manner as described above in the context of the meal probability model with respect to FIG. 9, the infusion device 102, 200, 502, 802 or the client device 106, 806 may obtain current measurement data values from the available sensing devices 104, 504, 506, 508, 804 and input the current measurement data values into the event prediction model to calculate a probability or likelihood of a particular event. In some embodiments, depending on the amount of measurement data to be input into the event prediction model, the infusion device 102, 200, 502, 802 or the client device 106, 806 may also buffer recent measurement data values preceding the current measurement data values (e.g., the preceding hour of measurement data) to facilitate detection of an event based on a trend or pattern in the recent measurement data. The event pattern control process 1000 may continually update the calculated probability for the event(s) being monitored for using the respective model(s) and detect or otherwise identify the occurrence of an event pattern in the patient's current or recent measurement data when the calculated probability for an event is greater than a threshold percentage or probability (e.g., greater than 75%).

In one or more embodiments, in response to detecting an event pattern, the application 608, 808 on the infusion device 102, 200, 502, 802 or the client device 106, 806 is configured to automatically adjust operation of the infusion device 102, 200, 502, 802 to account for the identified event. For example, in response to detecting a meal event, the application 608, 808 may automatically calculate a meal bolus amount based on a predicted meal size and/or a predicted meal content, and automatically command, signal, or otherwise instruct the command generation application 610 to operate the motor 532 to automatically deliver the bolus amount calculated based on the predicted meal size and/or predicted meal content. As another example, in response to detecting an exercise event, the application 608, 808 may automatically determine an adjusted target glucose value for the patient based on the type or intensity of exercise and the patient's historical glycemic response to that type of exercise event, and then automatically command, signal, or otherwise instruct the command generation application 610 to temporarily adjust the target glucose value 702 to the adjusted value that accounts for the patient's historical glycemic response to that type of exercise.

In the illustrated embodiment, prior to adjusting operation of the infusion device, the illustrated control process 1000 generates or otherwise provides a user notification that prompts the patient to confirm or otherwise verify the occurrence of the identified event before adjusting or otherwise modifying operation of the infusion device to account for the identified event based on the user response (tasks 1012, 1014). In this regard, an application 608, 808 on the infusion device 102, 200, 502, 802 or the client device 106, 806 may generate or otherwise provide a GUI display that indicates the type of event pattern that was detected. For example, the GUI display may indicate that a meal event was detected based on the patient's measurement data, and in some embodiments, the GUI display may include indication of the predicted meal size, the predicted meal content, and potentially other attributes of the meal predicted by the application 608, 808. In this regard, in some embodiments, the GUI display may also indicate a recommended action for responding to the detected event, such as, for example, a meal bolus amount, an adjusted target glucose value, or another adjustment to the patient's therapy that was calculated or otherwise recommended by the application 608, 808 based on the predicted event. Similarly, for an exercise event, the GUI display may include indication of the detected exercise intensity (e.g., anaerobic, aerobic, or the like) or the detected type of exercise, along with a corresponding therapy adjustment calculated or otherwise recommended by the application 608, 808 based on the type of exercise.

In exemplary embodiments, the GUI display includes a button or similar selectable GUI element that may be manipulated by the patient to confirm occurrence of the detected event and initiate the corresponding adjustment(s) to operation of the infusion device 102, 200, 502, 802. When the detected event is confirmed, a corresponding indication of a new event may be uploaded or otherwise provided to the remote device 108, 814 for uploading the patient's historical data to store data associated with the event along with the patient's recent measurement data for storing in association with the new event. The uploaded event and measurement data may then be utilized to dynamically update the event prediction model prior to the next iteration of the event pattern control process 1000. Alternatively, the GUI display may include GUI elements that allow the patient to invalidate the detected event or override or modify the therapy adjustments recommended by the application 608, 808. In this regard, when the event is confirmed but the therapy adjustments are modified, the patient's therapy modifications may be uploaded to the remote device 108, 814 along with the new event data and corresponding measurement data for dynamically updating or retraining any models utilized to generate therapy recommendations.

It should be noted that the event pattern control process 1000 may reduce or alleviate the patient burden of accounting for meals or other lifestyle events that may impact the patient's glucose level or insulin response, while also accounting for instances where the patient may otherwise delay or forget to adjust operation of the infusion device 102, 200, 502, 802 to account for the event. For example, when a meal event pattern is accurately detected, the patient may be prompted with a notification that identifies the predicted meal attributes and corresponding meal bolus amount, which the patient may confirm without having to perform carbohydrate counting or other calculations. Similarly, when an exercise event pattern is accurately detected, the patient may be prompted with a notification that identifies the predicted type of exercise and corresponding therapy adjustments, which the patient may confirm without having to manually characterize the exercise intensity or analyze how operation of the infusion device 102, 200, 502, 802 should be altered to account for the patient's estimation of his or her exercise intensity.

Moreover, it should be noted that the event pattern control process 1000 may be performed in concert with the prospective closed-loop control process 900 of FIG. 9 to improve the patient's glucose management. For example, prior to a meal event, the prospective closed-loop control process 900 may be performed to automatically increase the insulin delivery rate or insulin on board in advance of the meal, with the event pattern control process 1000 subsequently detecting the occurrence of a meal. Depending on the embodiment, the event pattern control process 1000 may then automatically administer a meal bolus for the predicted meal size and/or content, or alternatively, prompt the patient to confirm the meal and corresponding bolus. Additionally, the identification of a meal event by the event pattern control process 1000 may also be utilized to trigger or signal the prospective closed-loop control process 900 to revert to the original closed-loop control information once the meal bolus is confirmed and administered. Thus, when the meal is accurately predicted, the prospective closed-loop control process 900 and the event pattern control process 1000 cooperate to improve regulation of the patient's glucose and reduce the burden on the patient to count carbohydrates or manually configure the infusion device 102, 200, 502, 802 to administer a meal bolus or otherwise adjust operation. In a similar manner, the prospective closed-loop control process 900 and the event pattern control process 1000 may be utilized in concert to account for exercise, work, school, stress, or other activities or events that may influence the patient's insulin response or glucose level while also reducing the burden on the patient.

Personalized Bolus Process

Figure 11:
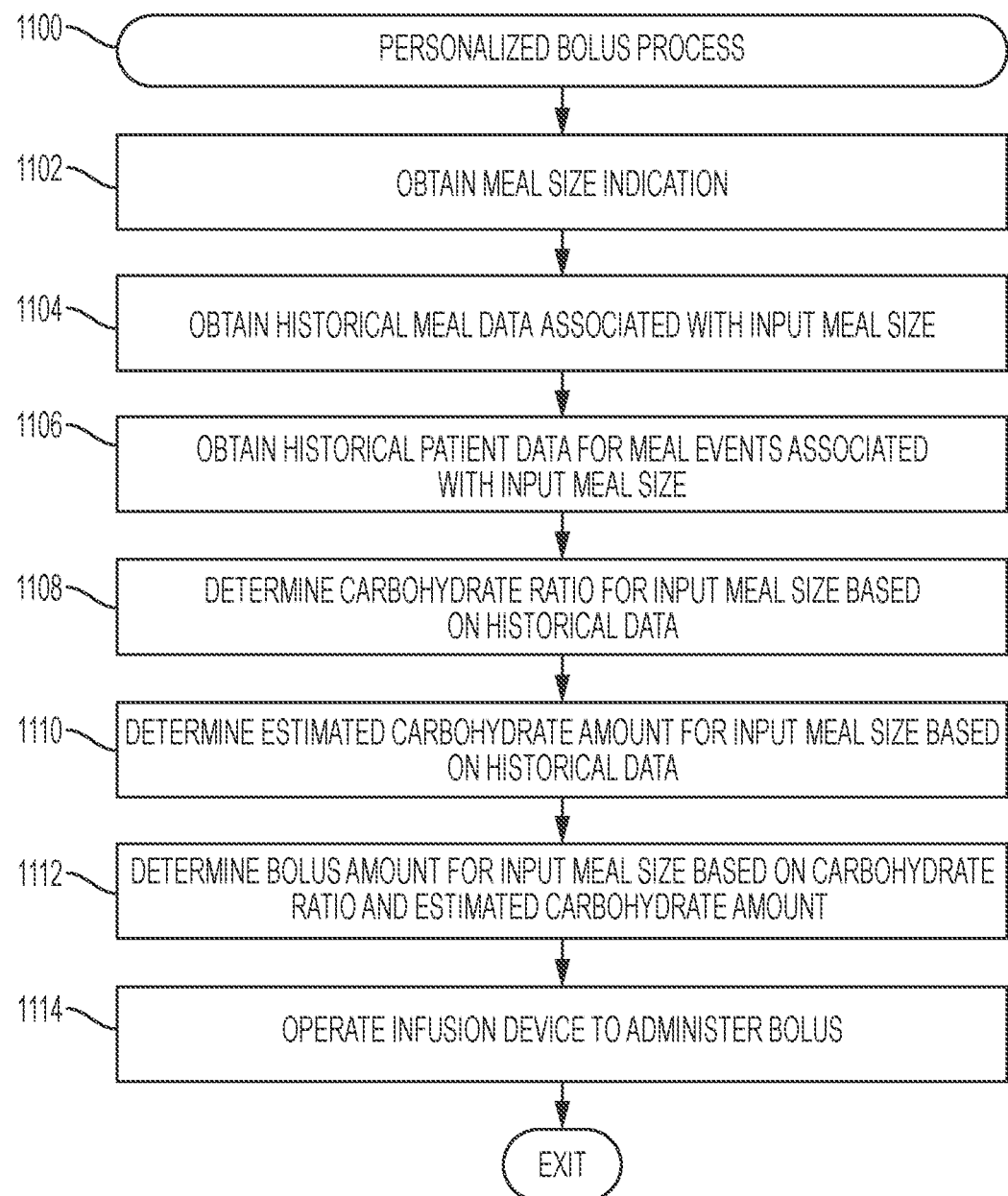
FIG. 11 is a flow diagram of an exemplary personalized bolus process suitable implementation in connection with an infusion device in one or more exemplary embodiments.

FIG. 11 depicts an exemplary personalized bolus process 1100 suitable for implementation by an infusion device (or a control system associated therewith) to determine a bolus amount in a personalized manner that reduces the burden associated with carbohydrate counting. In this regard, personalized bolus process 1100 allows for the patient to qualitatively define the size, content, or other aspects of a meal, with the qualitative user input being converted into a corresponding quantitative representation based on the patient's historical data. The quantitative representation is then utilized to determine a meal bolus dosage without requiring carbohydrate counting or other manual calculations or estimations.

The various tasks performed in connection with the personalized bolus process 1100 may be performed by hardware, firmware, software executed by processing circuitry, or any combination thereof. For illustrative purposes, the following description refers to elements mentioned above in connection with FIGS. 1-8. In practice, portions of the personalized bolus process 1100 may be performed by different elements of an infusion system, such as, for example, an infusion device 102, 200, 502, 802, a client computing device 106, 806, a remote computing device 108, 814, and/or a pump control system 520, 600. It should be appreciated that the personalized bolus process 1100 may include any number of additional or alternative tasks, the tasks need not be performed in the illustrated order and/or the tasks may be performed concurrently, and/or the personalized bolus process 1100 may be incorporated into a more comprehensive procedure or process having additional functionality not described in detail herein. Moreover, one or more of the tasks shown and described in the context of FIG. 11 could be omitted from a practical embodiment of the personalized bolus process 1100 as long as the intended overall functionality remains intact.

The illustrated personalized bolus process 1100 allows a patient to define meal sizes qualitatively, such as, for example, small, medium, large, extra large, and/or the like. In exemplary embodiments, personalized bolus process 1100 is implemented once sufficient historical meal data and corresponding patient measurement data has been obtained and stored in the database 816. For example, for an initial setup monitoring period, the patient may estimate or input meal sizes when logging meal events while also manually interacting with a bolus wizard or other feature of the infusion device 102, 200, 502, 802 or a client application 808 on the client device 106, 806 to configure and administer boluses for the contemporaneous meal events. In this regard, during the initial setup monitoring period, the patient may define or designate meals with a particular qualitative meal size while also performing carbohydrate counting and providing indication of the estimated carbohydrate amounts associated with those meals. Once the elapsed duration of the monitoring period is greater than a threshold setup period (e.g., 2 weeks) or a sufficient number of meal events have been logged or otherwise documented, the personalized bolus process 1100 may be enabled.

The personalized bolus process 1100 begins by receiving or otherwise obtaining an indication of a meal size for the meal to be bolused (task 1102). In one or more exemplary embodiments, the personalized bolus process 1100 is initiated when the patient interacts with a bolus wizard feature of a particular application 608, 610, 808 used to administer meal boluses. For example, the client application 808 at the client device 806 may generate or otherwise provide a bolus wizard GUI display that includes selectable GUI elements corresponding to different qualitative meal sizes, with the patient manipulating the client device 806 to select the meal size to be assigned to the current meal. In yet other embodiments, the personalized bolus process 1100 is automatically initiated in response to detecting a meal event pattern (e.g., task 1010) to calculate a meal bolus dosage based on the predicted meal, where the input meal size corresponds to the predicted meal size based on the patient's historical meal data, as described above.

In exemplary embodiments, the personalized bolus process 1100 receives or otherwise obtains the patient's historical meal data for historical meal events assigned or associated with the input meal size along with historical measurement data and historical insulin delivery data contemporaneous or concurrent to those historical meal events having the input meal size (tasks 1104, 1106). Based on the relationship between the historical meal data associated with the previous meal events and the corresponding historical patient measurement and insulin delivery data, the personalized bolus process 1100 calculates or otherwise determines a patient-specific carbohydrate ratio associated with the input meal size and a patient-specific carbohydrate amount associated with the input meal size (tasks 1108, 1110). In this regard, the patient-specific carbohydrate ratio accounts for variability of the actual meal size and other factors (e.g., time of day, day of the weak, nutritional components and consumption order for the meal, etc.) that affect the rate of glucose appearance. Similarly, the estimated carbohydrate amount associated with the input meal size may account for variations in the meal size based on the time of day, the day of the week, the geolocation, and other factors.

For example, in one or more embodiments, a mathematical model of the patient's postprandial glucose response to meals having the input meal size is created using the patient's historical sensor glucose measurement values for postprandial periods following the respective meal events, historical meal bolus dosages of insulin associated with the respective meal events, and historical closed-loop or basal insulin deliveries for postprandial and/or preprandial periods surrounding the respective meal events. An average or nominal glucose rate of appearance for the input meal size may be determined based on the historical sensor glucose measurement values and utilized to determine an estimated postprandial peak in the patient's sensor glucose value following a meal event. The mathematical model may then be optimized to identify an estimated carbohydrate ratio for the input meal size that results in an average estimated postprandial peak sensor glucose value at the estimated postprandial peak time following a meal event equal to a desired target postprandial peak sensor glucose value (e.g., 180 mg/dL). In other embodiments, a heuristic statistical analysis may be performed on the patient's historical meal, delivery, and measurement data to identify a carbohydrate ratio for the input meal size that is likely to achieve a desired postprandial glucose response. It should be noted that in some embodiments, the historical data sets utilized to determine the carbohydrate ratio may be further filtered or limited to be context-specific, for example, to particular periods of the day (e.g., meal events corresponding to a morning period between 6:00 A.M. and 12:00 P.M.), a particular day of the week, a particular geographic location, and/or the like.

In one or more exemplary embodiments, the mathematical model of the patient's postprandial glucose response to meals having the input meal size can describe the glucose response to insulin delivery and meal consumption by a set of ordinary differential equations. These equations may be based on a mass balance between estimated glucose utilization as result of insulin delivery and glucose increase as result of transformation of the meal into blood glucose. The mathematical model may also include specific parameters that enable it to predict the blood glucose at fasting. The mathematical model of the patient's specific meal response may be adjusted using curve fitting, for example, by adjusting the meal absorption rates in the mathematical model to fit the measured historical glucose curve and thereby establish the most proper meal absorption rates.

In one or more embodiments, to determine a patient-specific carbohydrate amount associated with the input meal size, machine learning or another artificial intelligence technique is utilized to probabilistically model the estimated carbohydrates associated with an input meal size as a function of the time of the day, the day of the week, and potentially other context or factors (e.g., the current geographic location, the current sensor glucose measurement value, or the like) using the patient's historical meal data and corresponding context information, historical measurement data, and/or historical delivery data. For example, an equation for calculating a probable carbohydrate value as a function of the input meal size and other correlative or predictive variables may be determined and utilized to map the patient's input meal size to a probable carbohydrate amount given the current operational context. In this manner, the personalized bolus process 1100 accounts for patient-specific variations in the manner in which the patient qualitatively assesses meal size. For example, based on the data collected during the initial setup monitoring period, if a patient tends to characterize a meal having roughly the same amount of carbohydrates as different sizes depending on the time of the day or the day of the week, the patient-specific quantitative meal size model may be configured to increase or decrease the output carbohydrate estimation accordingly.

In yet other embodiments, a patient-specific carbohydrate amount associated with the input meal size may be determined heuristically based on a statistical analysis of the carbohydrate amounts associated with the historical meal events having the input meal size. For example, the estimated carbohydrate amount associated with the input meal size may be determined as the average of the carbohydrate amounts associated with the input meal size during the initial setup monitoring period. As another example, the estimated carbohydrate amount associated with the input meal size may be determined probabilistically based on the distribution of the input carbohydrate amounts associated with the input meal size between the minimum input carbohydrate amount and the maximum input carbohydrate amount.

Still referring to FIG. 11, once a carbohydrate ratio and estimated carbohydrate amount associated with the input meal size for the current operating context are determined, the personalized bolus process 1100 continues by calculating or otherwise determining a meal bolus dosage amount using the carbohydrate ratio and the estimated carbohydrate amount and operating the infusion device to administer the meal bolus dosage amount (tasks 1112, 1114). In this regard, the estimated carbohydrate amount for the input meal size is multiplied by the carbohydrate ratio for the input meal size to obtain a corresponding bolus dosage to be administered. The command generation application 610 is then commanded, signaled, or otherwise instructed to operate the motor 532 of the infusion device 502 to deliver the calculated bolus dosage of insulin. In some embodiments, the calculated meal bolus dosage may be automatically administered; however, in other embodiments, a notification of the calculated meal bolus dosage may be generated or otherwise provided on a GUI display for review, modification, and/or confirmation by the patient. Such a GUI display may also include indication of the estimated carbohydrate ratio and estimated carbohydrate amount determined by the personalized bolus process 1100 for review, modification, and/or confirmation. In this regard, some embodiments may allow the patient to override the personalized bolus process 1100 and modify one or more of the carbohydrate ratio, the carbohydrate amount, or the bolus dosage amount. In such scenarios, the patient modifications may be utilized to update or otherwise adjust the models for estimating the patient's carbohydrate ratio and/or carbohydrate amount to be associated with the input meal size for subsequent iterations of the personalized bolus process 1100.

By virtue of the carbohydrate ratio and the estimated carbohydrate amounts being personalized and context-specific based on the patient's historical meal, delivery, and measurement data, the meal bolus accounts for variations in the rate of glucose appearance for the patient along with variations in the actual quantitative meal size relative to the input qualitative meal size. This allows the patient to merely input a qualitative meal size rather than having to resort to carbohydrate counting while still providing a meal bolus dosage that maintains safe and effective postprandial glucose management.

It should be noted that the personalized bolus process 1100 may be performed in concert with the prospective closed-loop control process 900 and the event pattern control process 1000 to improve the patient's glucose management. In this regard, as described above, the prospective closed-loop control process 900 automatically increases the insulin delivery rate or insulin on board in advance of the meal. The personalized bolus process 1100 may then be initiated automatically at the predicted meal time or in response to the event pattern control process 1000 detecting the occurrence of a meal. The personalized bolus process 1100 then determines a personalized, context-specific meal bolus dosage corresponding to the meal size that was automatically identified, detected, or predicted. The patient may then simply confirm the detected meal size and trigger administration of the meal bolus amount with as little as a single user input without any carbohydrate counting or other manual interaction. Additionally, by virtue of the prospective closed-loop adjustments and the carbohydrate ratio that is personalized and specific to the current meal size and operational context, variations in the rate of glucose appearance, non-homogeneity of meals, and other factors can be accounted for or otherwise mitigated to improve efficacy of postprandial glucose management.

Personalized Bolusing Using Nutritional Content

Figure 12:
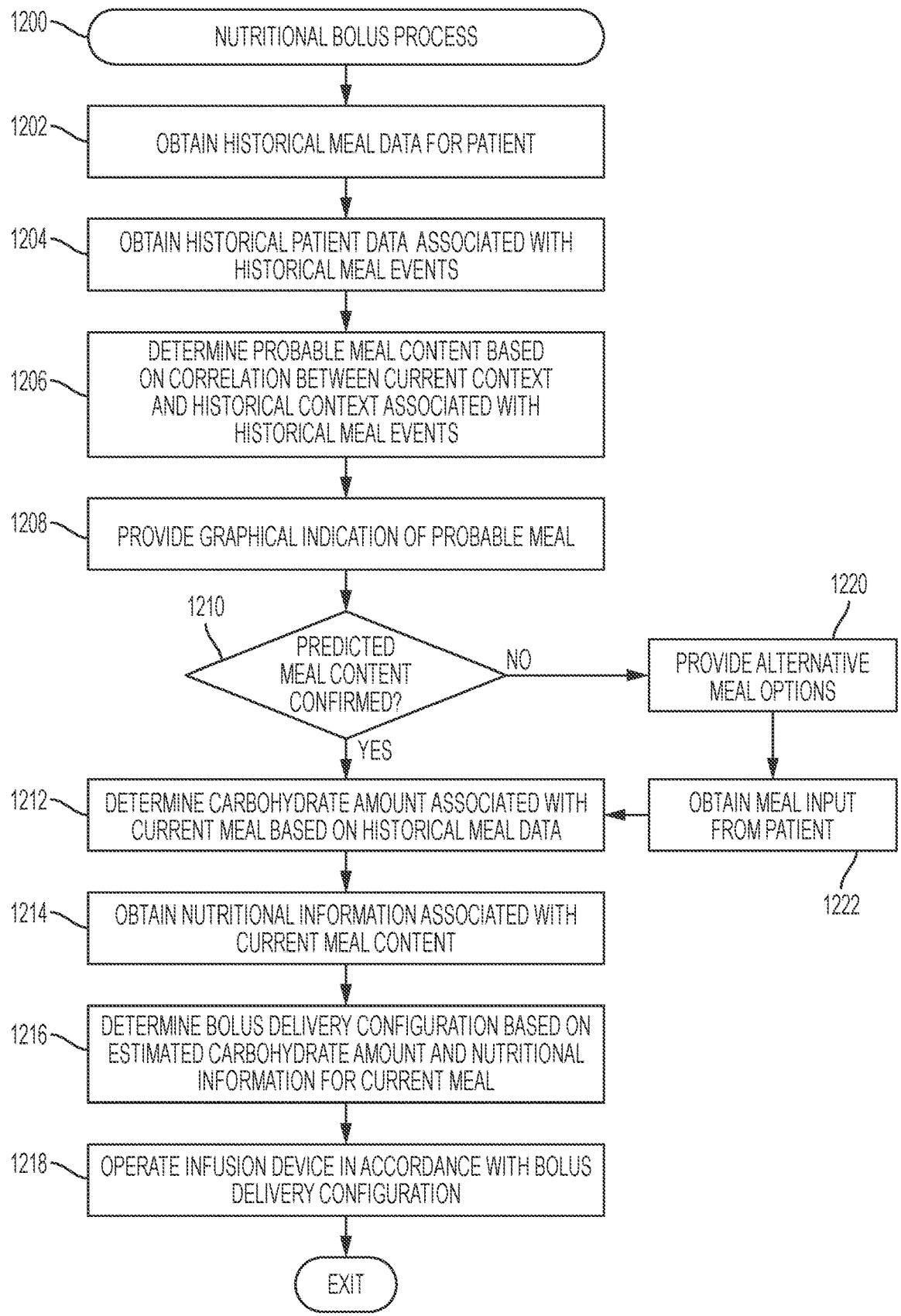
FIG. 12 is a flow diagram of an exemplary nutritional bolus process suitable implementation in connection with an infusion device in one or more exemplary embodiments.

FIG. 12 depicts an exemplary nutritional bolus process 1200 suitable for implementation by an infusion device (or a control system associated therewith) to determine a bolus amount based on the nutritional content of a meal in a personalized manner that reduces the burden associated with carbohydrate counting. In this regard, nutritional bolus process 1200 allows for the patient to define the nutritional content or type of meal being consumed, with a corresponding bolus amount being determined based on nutritional characteristics of the meal and the patient's historical data. The various tasks performed in connection with the nutritional bolus process 1200 may be performed by hardware, firmware, software executed by processing circuitry, or any combination thereof. For illustrative purposes, the following description refers to elements mentioned above in connection with FIGS. 1-8. In practice, portions of the nutritional bolus process 1200 may be performed by different elements of an infusion system, such as, for example, an infusion device 102, 200, 502, 802, a client computing device 106, 806, a remote computing device 108, 814, and/or a pump control system 520, 600. It should be appreciated that the nutritional bolus process 1200 may include any number of additional or alternative tasks, the tasks need not be performed in the illustrated order and/or the tasks may be performed concurrently, and/or the nutritional bolus process 1200 may be incorporated into a more comprehensive procedure or process having additional functionality not described in detail herein. Moreover, one or more of the tasks shown and described in the context of FIG. 12 could be omitted from a practical embodiment of the nutritional bolus process 1200 as long as the intended overall functionality remains intact.

Similar to the personalized bolus process 1100, the nutritional bolus process 1200 may be manually initiated when the patient interacts with a bolus wizard feature of a particular application 608, 610, 808 used to administer meal boluses, or automatically initiated in response to detecting a meal event pattern. The illustrated nutritional bolus process 1200 receivers or otherwise obtains the patient's historical meal data along with historical measurement data and historical insulin delivery data contemporaneous or concurrent to historical meal events (tasks 1202, 1204). Based on the relationship between the historical meal data associated with the previous meal events and the corresponding context associated with the historical meal events, the nutritional bolus process 1200 calculates or otherwise determines the probable meal content given the current operational context (task 1206). In this regard, the nutritional bolus process 1200 probabilistically predicts what the patient is likely to be consuming given the current time of day, the current day of the week, the patient's current glycemic status or activity status, and the like based on the patient's historical meal behavior. The nutritional bolus process 1200 generates or otherwise provides an indication of the most probable meal content for confirmation or acceptance by the patient (tasks 1208, 1210). In one or more embodiments, a notification of the predicted meal content having the highest or greatest probability is generated or otherwise provided on a GUI display for review, modification, and/or confirmation by the patient. In other embodiments, a listing of a subset of potential meal contents having the highest or greatest probabilities for the current context are presented on a GUI display for perusal or selection by the patient. In this regard, the listing of the potential meal content options is personalized and reflects the patient's historical meal behavior.

For example, for an initial setup monitoring period, the patient may select or otherwise indicate the nutritional content, type, or components of a meal when logging meal events while also manually interacting with a bolus wizard or other feature of the infusion device 102, 200, 502, 802 or a client application 808 on the client device 106, 806 to configure and administer boluses for the contemporaneous meal events. During the initial setup monitoring period, the patient may also perform carbohydrate counting and provide indication of the estimated carbohydrate amounts associated with those meals. Once the elapsed duration of the monitoring period is greater than a threshold setup period or a sufficient number of meal events have been logged or otherwise documented, the nutritional bolus process 1200 may be enabled. Based on the correlation between one or more of the current time of day, the current day of the week, the current geographic location, the current or recent sensor glucose measurement values, the current or recent acceleration measurement values, the current or recent heart rate measurement values, and potentially other context information with respect to the context information associated with the patient's historical meal events, the nutritional bolus process 1200 determines what the most probable meal content is for the current operational context. The nutritional bolus process 1200 then generates or otherwise provides a GUI display at the infusion device 102, 200, 502, 802 or the client device 106, 806 that includes one or more predicted meal types having the highest probability or likelihood given the current operational context.

In the illustrated embodiment, in response to selection or confirmation of the predicted meal content, the nutritional bolus process 1200 continues by calculating or otherwise determining an estimated carbohydrate amount associated with the current meal nutritional content (task 1212). In this regard, based on the patient's historical meal events having the same type, composition, or nutritional content, any carbohydrate amounts input or otherwise provided by the patient during the initial setup monitoring period may be averaged or otherwise analyzed to determine a probable carbohydrate amount associated with the current meal content based on the patient's historical meal sizes for that type of meal. In some embodiments, the historical meal data for the current meal content may be further limited or analyzed in a context specific manner to account for variations in the size of that type of meal depending on the current time of day, the current day of the week, or other operational contexts. In yet other embodiments, an estimated carbohydrate amount associated with the current meal content may be calculated or determined based on the relationship between the patient's historical insulin delivery data and sensor glucose measurement data for historical meal events with the common meal content.

The nutritional bolus process 1200 also receives or otherwise obtains nutritional information associated with the current meal content and calculates or otherwise determines a meal bolus delivery configuration based on the nutritional characteristics of the current meal content and the estimated carbohydrate amount for the current meal (tasks 1214, 1216). In this regard, the nutritional bolus process 1200 may adjust bolus dosage amounts or bolus delivery schedules in a manner that accounts for the postprandial glycemic response to the nutritional content of the meal. Additionally, the bolus delivery configuration may also involve modifying closed-loop control information in concert with an adjusted bolus dosage amount to further improve postprandial glucose management given the nutritional content of the meal. After determining the meal bolus delivery configuration that accounts for the nutritional characteristics of the meal, the nutritional bolus process 1200 operates the infusion device in accordance with the bolus delivery configuration (task 1218).

For example, the remote device 814 and/or the database 816 may store nutritional information associated with different types of meals or nutritional content, such as, for example, a serving size or unit, the amount of carbohydrates per serving size, the amount of fat per serving size, the amount of protein per serving size, the amount of calories per serving size, the amount of fiber per serving size, the amount of sodium per serving size, and the like. An application 608, 808 at one of the infusion device 102, 200, 502, 802 or the client device 106, 806 may retrieve or otherwise request the nutritional information associated with the current meal content from the remote device 814, and then utilize the nutritional information and the estimated meal size to calculate or determine a complete nutritional profile for the meal being consumed. The application 608, 808 then calculates or otherwise determines a meal bolus dosage amount that based on the estimated carbohydrate amount that is also adjusted to account for the relationship between the amount of carbohydrates, fat, protein, fiber, and/or other nutritional attributes of the current meal. The application 608, 808 may also identify or otherwise determine one or more modifications to the closed-loop control parameters utilized by the closed-loop control system 700 supported by the command generation application 610. The application 608, 808 then commands, signals, or otherwise instructs the command generation application 610 to deliver the adjusted meal bolus dosage amounts according to the desired bolus schedule, and depending on the particular embodiment, also temporarily modify one or more control parameters utilized by the closed-loop control system 700 supported by the command generation application 610 for a postprandial period.

For example, for meal content that consists of more fast acting carbohydrates relative to the amount of fat, fiber, or the like (e.g., a sugary or high carbohydrate breakfast), the application 608, 808 may scale a bolus dosage amount determined by multiplying the estimated carbohydrate amount by a carbohydrate ratio by a factor greater than one to increase the meal bolus amount while also commanding, signaling, or otherwise instructing the command generation application 610 to temporarily suspend delivery by the closed-loop control system 700. Conversely, for meal content that consists of more fat relative to the amount of carbohydrates, the application 608, 808 may scale a bolus dosage amount determined by multiplying the estimated carbohydrate amount by a carbohydrate ratio by a factor less than one to decrease the meal bolus amount while also commanding, signaling, or otherwise instructing the command generation application 610 to temporarily utilize a lower target glucose value 702 and/or increase the minimum and/or maximum basal rate settings to gradually increase insulin delivery during the postprandial period to better account for the meal content. It should be noted that the manner or amount of adjustments to the bolus dosage amount or postprandial closed-loop control adjustments may be personalized or patient-specific and influenced by relationships between the patient's historical postprandial sensor glucose measurements and insulin deliveries associated with historical meal events having common nutritional content.

Still referring to FIG. 12, when the probable meal content is overruled or otherwise not accepted by the patient, the illustrated nutritional bolus process 1200 generates or otherwise provides a listing of one or more alternative meals that are selectable by the patient (task 1220). In this regard, a personalized, patient-specific library of potential meal content may be created based on the patient's historical meal data and utilized to present additional meal options to the patient. For example, when the most probable meal content originally displayed by the nutritional bolus process 1200 is not confirmed by the patient, the nutritional bolus process 1200 may provide a listing or library of meal content corresponding to one or more of the patient's historical meal events sorted in descending order according to their respective probabilities or likelihoods given the current operational context (e.g., time of day, day of week, current sensor glucose measurement value, current geographic location, and/or the like). Thus, the number of user inputs required by the user to select the appropriate meal content may be reduced by presenting meal content options that are known to have been consumed by the patient. The nutritional bolus process 1200 receives user input indicative of the current meal content (task 1222) and continues by determining a meal bolus delivery configuration for the input meal content in a similar manner as described above. For example, the patient may scroll the personalized list of meal content and select the current meal content from the list, and in response, historical meal data corresponding to the selected meal content is analyzed to identify the estimated meal size or number of servings being consumed in a similar manner as described above.

In one or more embodiments, the nutritional bolus process 1200 may be configured to allow the patient to input or otherwise indicate the meal content by uploading a photograph or image of the meal being consumed. In this regard, either the client application 808 at the client device 806 or the remote device 814 may support object recognition or other image processing artificial intelligence that allows a submitted or uploaded photograph to be mapped to a particular type of meal content. In one or more embodiments, the client application 808 at the client device 806 or the remote device 814 may support a neural network model or similar artificial intelligence model that is trained using images corresponding to the patient's historical meal data, so that the recognition accuracy is improved for uploaded images of meal content previously consumed by the patient.

Similar to the personalized bolus process 1100 of FIG. 11, the nutritional bolus process 1200 allows the patient to merely confirm the most probable meal content or provide indication of an alternative without having to resort to carbohydrate counting, meal size estimation, and/or the like. It should be noted that the nutritional bolus process 1200 may be performed in concert with the prospective closed-loop control process 900 and the event pattern control process 1000 to improve the patient's glucose management. In this regard, as described above, the prospective closed-loop control process 900 automatically increases the insulin delivery rate or insulin on board in advance of the meal. The nutritional bolus process 1200 may then be initiated automatically at the predicted meal time or in response to the event pattern control process 1000 detecting the occurrence of a meal. The nutritional bolus process 1200 then determines a personalized, context-specific meal bolus delivery configuration corresponding to the nutritional content of the meal that was automatically identified, detected, or predicted. The patient may then simply confirm the predicted meal content and trigger administration of a meal bolus with as little as a single user input without any carbohydrate counting or other manual interaction. Additionally, in embodiments where closed-loop adjustments are also performed according to the nutritional content of the meal, variations in the rate of glucose appearance depending on the meal content can be accounted for or otherwise mitigated to improve efficacy of postprandial glucose management. It should be noted that the nutritional bolus process 1200 may also be performed in concert with the personalized bolus process 1100, for example, to further adjust or refine the personalized meal bolus amount for the current meal size (e.g., from task 1112) or adjust closed-loop control information for a postprandial period to account for the nutritional content or components of the meal, and thereby improve postprandial glucose management.

Personalized Adjustments for Patient Activity

Figure 13:
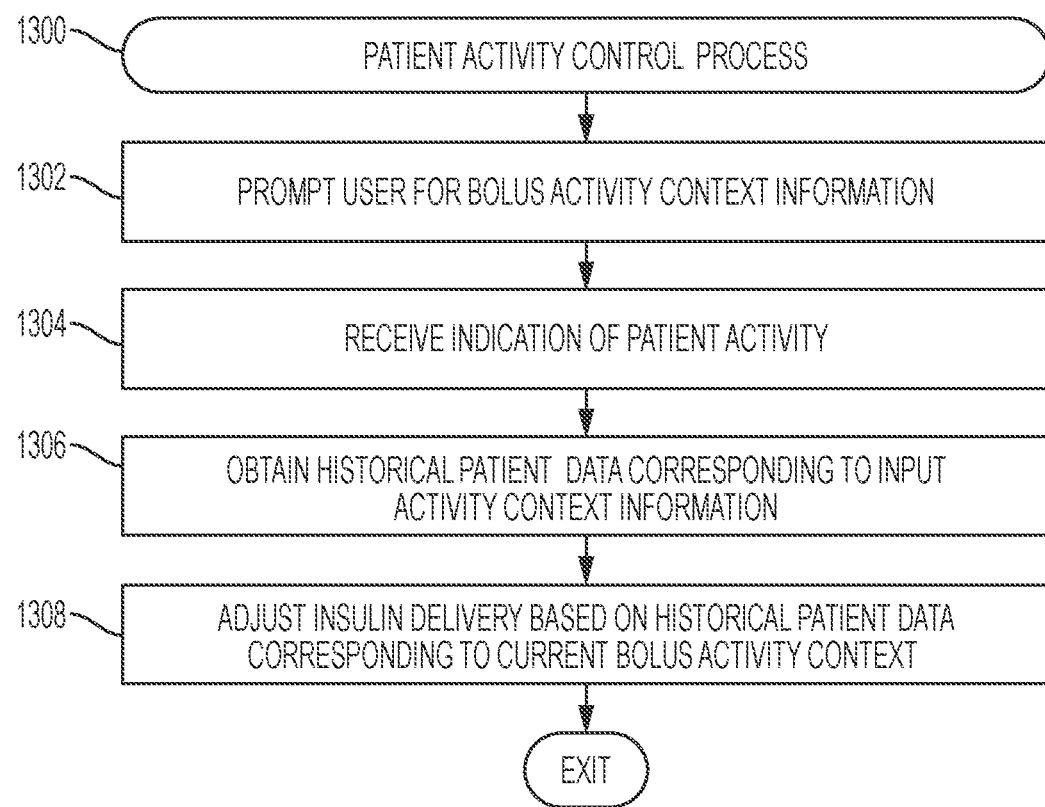
FIG. 13 is a flow diagram of an exemplary patient activity control process suitable implementation in connection with an infusion device in one or more exemplary embodiments.

FIG. 13 depicts an exemplary patient activity control process 1300 suitable for implementation by an infusion device (or a control system associated therewith) to adjust a bolus amount or closed-loop control information for a postprandial period in a personalized manner that accounts for activity that the patient is or will be engaged in. In this regard, patient activity control process 1300 allows for the patient to indicate what activity or activities the patient is or will be engaged in that could influence his or her insulin response, which, in turn may be utilized to increase or decrease insulin delivery in a personalized manner based on the historical effects of that activity on the patient's glycemic status.

The various tasks performed in connection with the patient activity control process 1300 may be performed by hardware, firmware, software executed by processing circuitry, or any combination thereof. For illustrative purposes, the following description refers to elements mentioned above in connection with FIGS. 1-8. In practice, portions of the patient activity control process 1300 may be performed by different elements of an infusion system, such as, for example, an infusion device 102, 200, 502, 802, a client computing device 106, 806, a remote computing device 108, 814, and/or a pump control system 520, 600. It should be appreciated that the patient activity control process 1300 may include any number of additional or alternative tasks, the tasks need not be performed in the illustrated order and/or the tasks may be performed concurrently, and/or the patient activity control process 1300 may be incorporated into a more comprehensive procedure or process having additional functionality not described in detail herein. Moreover, one or more of the tasks shown and described in the context of FIG. 13 could be omitted from a practical embodiment of the patient activity control process 1300 as long as the intended overall functionality remains intact.

The patient activity control process 1300 begins by generating or otherwise prompting the patient to define the current operational context for a bolus in terms of the activity that the patient is or will be engaged in and receiving or otherwise obtaining indication of one or more activities that the patient is or will be engaged in from the patient (tasks 1302, 1304). In one or more exemplary embodiments, the patient activity control process 1300 is initiated during patient interaction with a bolus wizard feature or other GUI display that is utilized to configure or administer meal boluses. For example, the client application 808 at the client device 806 may generate or otherwise provide a GUI display that includes a list of selectable GUI elements corresponding to different activities that the patient could engage in after the patient has input or confirmed information characterizing the current meal to be bolused. For example, the patient activity control process 1300 may be performed in concert with the personalized bolus process 1100 after confirming the size of the meal to be bolused and/or in concert with the nutritional bolus process 1200 after confirming the nutritional content of the meal to be bolused. The GUI display then presented by the client application 808 at the client device 806 may include selectable GUI elements corresponding to exercise, sleep, work, stress, travel, or other types of activities that the patient might engage in in the immediate future. Moreover, the GUI display may be configured to allow the patient to select or define attributes or characteristics associated with those activities, such as, for example, the intensity or type of exercise (e.g., aerobic, anaerobic, cardio, strength training, and/or the like), the duration of time the patient intends to sleep (e.g., whether the sleep corresponds to an overnight period or a nap), and/or the like. The patient may then manipulate the GUI elements on the GUI display to indicate and define the activity that the patient is currently engaged in contemporaneous to the meal bolus or will be engaged in thereafter.

Based on the input activity, the patient activity control process 1300 retrieves or otherwise obtains historical patient data corresponding to historical events matching that activity and then adjust or modifies current or future insulin deliveries based on the patient's historical glycemic response to the activity (tasks 1306, 1308). In this regard, an application 608, 808 at one of the infusion device 102, 200, 502, 802 or the client device 106, 806 may retrieve or otherwise request historical sensor glucose measurement data and historical insulin delivery data contemporaneous or concurrent to past occurrences of the input activity. For example, the client application 808 may support the patient logging or journaling various activities or lifestyle events and uploading the event log data to the remote device 814 for storage in the database 816. The event log data may include a time or timestamp associated with the particular activity or event, the day of the week associated with the activity or event, its associated geolocation, the duration of the activity, and potentially other attributes of the activity. The application 608, 808 at one of the infusion device 102, 200, 502, 802 or the client device 106, 806 may request event log data associated with activities or events that match the input activity, and then utilize the temporal information associated with those historical events (e.g., timestamps and durations) to select corresponding subsets of the patient's historical measurement data and insulin delivery data contemporaneous or concurrent to those historical events. The relationship between the patient's historical measurement data and insulin delivery data corresponding to the historical occurrences of the input activity may be modeled or otherwise analyzed to determine the patient's average or likely glycemic response to the input activity, for example, by comparing the relationships between the subsets of the patient's historical measurement data and the insulin delivery data corresponding to the historical occurrences to the relationships between the patient's historical measurement data and insulin delivery data generally. For example, the patient's historical glycemic response when the patient engaged in a particular type of exercise within a threshold period of time after a meal may be compared to when the patient's historical glycemic response when the patient did not engage in exercise within that time period after a meal.

Once the patient's historical glycemic response to the input activity is quantified or otherwise characterized, the application 608, 808 supporting the patient activity control process 1300 automatically adjusts the bolus delivery configuration in a manner that corresponds to the patient's historical glycemic response to the input activity. For example, if the relationship between the patient's historical measurement data and insulin delivery data corresponding to the historical occurrences of the input activity indicate that the patient's glycemic response requires roughly 20% less insulin delivered than when the patient does not engage in the activity, the application 608, 808 may automatically reduce the calculated meal bolus amount by 20% or adjust one or more closed-loop control parameters for the postprandial period to reduce the insulin delivery by roughly 20%. In this manner, the likelihood of postprandial hypoglycemia or a need to subsequently consume additional carbohydrates may be reduced. Similarly, if the patient's historical glycemic response indicates more insulin is required to avoid postprandial hyperglycemia, the bolus amount or closed-loop control information may be adjusted to increase insulin delivery to avoid postprandial hyperglycemia or subsequent correction boluses.

In one or more exemplary embodiments, machine learning or other modeling is utilized to predict one or more characteristics of the patient's future activity, which, in turn, may be utilized to determine the probable glycemic response and corresponding amount or duration of insulin delivery adjustments to be made in a manner that is influenced by the predicted characteristics of the future activity. For example, an expected duration, an expected intensity, and/or other attributes of the future activity may be predicted by determining which combinations or subsets of historical measurement data, historical event log data, and historical operational contexts (e.g., time of day, day of week, geographic location, and the like) are correlative or predictive of the intensity, duration, or other characteristic or attribute of a particular activity. A corresponding equation, function, or model for calculating a metric or value representative of the duration, intensity, or other characteristic for the future activity may be determined that may then be applied to the current operational context or the future operational context associated with the future activity to determine the expected duration, intensity, or other characteristic given the current operational context or the future operational context.

For example, the duration or intensity associated with historical exercise events may be utilized to construct a model that allows the application 608, 808 supporting the patient activity control process 1300 to predict an expected duration or intensity for an anticipated future exercise event as a function of the time of day, the day of the week, the geographic location, current or recent sensor glucose measurements, current or recently logged events, and/or the like. Similarly, a model may also be constructed that models the patient's glycemic response to a particular duration or intensity of exercise as a function of the current time of day (or a future time of day associated with the anticipated exercise event), the current day of the week, the current geographic location, current or recent sensor glucose measurements, current or recently logged events, and/or the like based on correlations between historical operational contexts and historical sensor glucose measurements associated with historical exercise events having similar durations or intensities. The model appropriate for the predicted duration or intensity for the future exercise event may thus be utilized to determine the probable glycemic response, which, in turn, is utilized to adjust bolus dosages amounts or schedules or closed-loop control parameters in an appropriate manner. A model may also be developed that allows for a predicted future time of day in advance of the current time to be calculated based at least in part on the historical times of day associated with previous exercise events, with the predicted future time of day then being input to another model for predicting exercise characteristics or glycemic response based on when the future exercise event is most likely to occur.

Similarly, when the future activity by the patient is sleeping, the duration associated with previous sleep events may be utilized to construct a model that allows the application 608, 808 to predict an expected duration of sleep as a function of the time of day (e.g., napping versus overnight), the day of the week, the geographic location, and potentially other contextual factors. Similarly, the patient's glycemic response during sleep may be modeled in a manner that accounts for the duration of sleep, the current time of day, the current day of the week, the current geographic location, current or recent sensor glucose measurements, current or recently logged events, and/or the like. It should be noted that in some embodiments, the expected duration for a future sleep event may be utilized to influence the duration of insulin delivery adjustments that are implemented by the patient activity control process 1300. For example, a target glucose value or other closed-loop control parameter may be maintained at an adjusted value for a duration of time configured to overlap with or otherwise correspond to the duration of time during which the user is expected to be sleeping before reverting to the original, preceding, or unadjusted value. In a similar manner, adjustments for an exercise event may be configured to temporarily align with the expected duration of the exercise before reverting to their preceding state or value.

It should be noted that the patient activity control process 1300 may be performed in concert with any or all of the processes described above in the context of FIGS. 9-12 to adjust bolus amounts or closed-loop control information in anticipation of subsequent patient activity and cooperatively improve glucose management. For example, the prospective closed-loop control process 900 may proactively load insulin in advance of a meal, which subsequently be detected by the event pattern control process 1000, which, in turn, triggers the personalized bolus process 1100 and/or the nutritional bolus process 1200 to determine meal bolus dosage amounts and any other closed-loop control adjustments for a postprandial period. The patient activity control process 1300 may then be performed to further modify the meal bolus dosage amount or closed-loop control parameters determined by the personalized bolus process 1100 and/or the nutritional bolus process 1200 to account for the anticipated patient activity, thereby improving postprandial glucose management. It should be noted that the event pattern control process 1000 may subsequently detect occurrence of the anticipated patient activity, and further fine tune or adjust closed-loop control parameters at that time. In such scenarios, the patient activity control process 1300 effectively performs prospective adjustments to the patient's insulin delivery before any real-time adjustments that may be performed in connection with the event pattern control process 1000 to further improve glucose management throughout the duration of the activity.

While the patient activity control process 1300 may be primarily described in the context of modifications that account for future events or activities, the patient activity control process 1300 may be implemented in an equivalent manner for contemporaneous, concurrent, or preceding events or activities. Thus, the patient activity control process 1300 may be able to proactively account for past or current activities or events that have not yet exhibited a corresponding glycemic response in advance of any potential glucose excursions.

Referring to FIG. 8 with reference to FIGS. 9-13, it should be noted that in one or more embodiments, various aspects of the processes of FIGS. 9-13 may be distributed across different devices in a patient monitoring system 800. For example, sensor glucose measurement data and other measurement data pertaining to the patient may be periodically uploaded from a medical device 802, such as a sensing arrangement 104, 504, 506 or an infusion device 102, 200, 502, to the remote device 814 (either directly or indirectly by way of an intermediary device 806) for storage in the database 816 in association with the patient. Similarly, event log data including meal indicia, exercise indicia, and other information characterizing events and lifestyle activities may be uploaded from the client application 808 at the client device 806 to the remote device 814 for storage in the database 816 in association with the patient.

The remote device 814 may then periodically analyze the relationships between the patient's measurement and event log data to generate personalized patient-specific models, for example, on a daily basis, a weekly basis, a biweekly basis, a monthly basis, or the like. The remote device 814 may generate various patient-specific models for different operational contexts (e.g., for different times or periods of the day, for different days of the week, for different geographic locations or regions, and the like) and dynamically update the models on a periodic basis using machine learning or other artificial intelligence techniques to account for recent measurement and event log data added to the database 816 since the models were previously generated and adaptively track changes in the patient's behavior.

Depending on the embodiment, the remote device 814 may store or maintain the models in the database 816 in association with the patient for subsequent retrieval by a device 802, 806 associated with the patient, or alternatively, the remote device 814 may automatically push updated models to one or more devices 802, 806 associated with the patient. The infusion device 802 or the client device 806 associated with the patient may then select or otherwise identify the appropriate patient-specific models provided by the remote device 814 for the current operational context and then utilize those models to support the processes of FIGS. 9-13 described above. For example, in response to the patient manipulating the client application 808 to add a meal, exercise, or other activity to his or her event log, the client application 808 may select the appropriate models or functions for generating the appropriate bolus dosage amounts or control adjustments given the current operational context and responsive to user inputs received via the client application 808 (e.g., indicia of meal size, meal content, postprandial activities, and/or the like). The client application 808 may then transmit or otherwise provide corresponding commands, signals, or instructions to the infusion device 802, which, in turn, alters insulin delivery in a patient-specific and context-sensitive manner as described above. In yet other embodiments, the remote device 814 may receive current or recent measurement and/or event log data from one or more of the devices 802, 806, apply the appropriate patient-specific models to the current or recent data at the remote device 814 to determine commands for altering or adjusting operation of the infusion device 802, and then transmitting or otherwise providing such commands to the infusion device 802 (e.g., via the client device 806). Thus, depending on the embodiment, the control system associated with the infusion device 802 that is supporting or otherwise implementing a respective process of FIGS. 9-13 could reside at any one of the devices 802, 806, 814.

It should be noted that in one or more embodiments, the patient model may be normalized or augmented using broader population data. For example, a population model may be developed by the remote device 814 by analyzing relationships between measurement data, event log data, and operational context across a plurality of different patients. In some embodiments, patients may be assigned or otherwise associated with a particular group of patients having one or more characteristics in common based on the demographic information associated with that patient, with a probabilistic predictive model for that patient group being determined based on the aggregated historical data for the different patients of the group. In this regard, in the absence of sufficient historical data in the database 816 for a particular patient, a model associated with that patient's population group may be utilized to predict the patient's behavior and/or the patient's likely glycemic response. As the amount of historical data associated with the patient increases, the remote device 814 may transition to determining and pushing patient-specific models to the patient's associated device(s) 802, 806. In this regard, in some embodiments, a result, outcome, or output produced using a patient-specific model may be progressively weighted or otherwise combined with a corresponding result, outcome, or output produced using a population group model in accordance with the amount of available historical data associated with that patient in a manner that reflects the level of accuracy, reliability, or confidence in the patient-specific model until a threshold amount of historical data is obtained that allows sole reliance on the patient-specific model.

Figure 15:
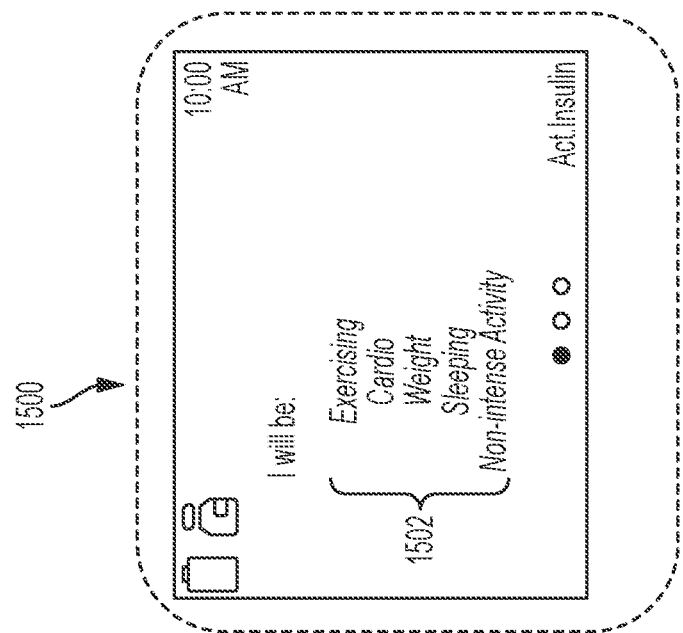
FIGS. 14-15 depict exemplary graphical user interface displays that may be presented on an electronic device in connection with one or more of the processes of FIGS. 9-13.
Figure 14:
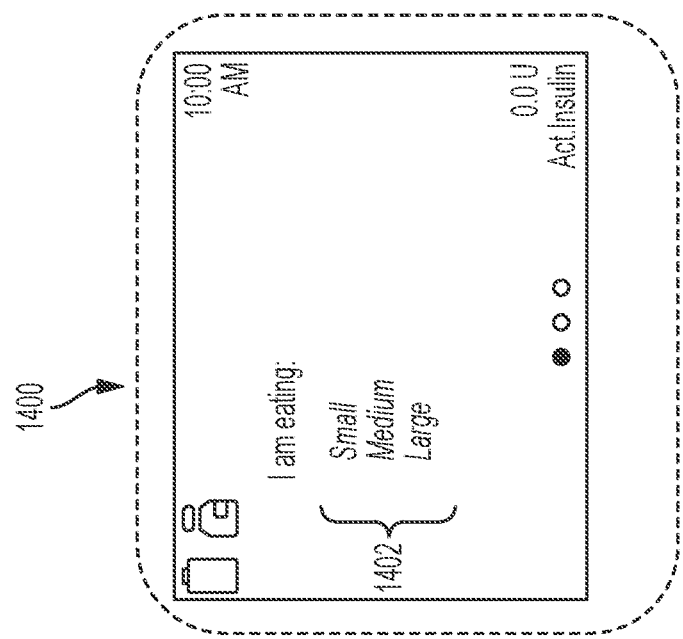

FIGS. 14-15 depict one exemplary sequence of GUI displays that may be presented on an electronic device in accordance with one or more of the processes of FIGS. 9-13 described above. For example, FIG. 14 depicts a meal size GUI display 1400 that may be presented by the client application 808 on the computing device 806 to enable the patient to input the size of a meal to be bolused for. In some embodiments, the meal size GUI display 1400 is automatically presented at a predicted meal time or when the probability of a meal being consumed at the current time is greater than a threshold probability (e.g., greater than 75%). In other embodiments, the meal size GUI display 1400 is automatically presented in response to detecting a meal event pattern. In yet other embodiments, the meal size GUI display 1400 may be presented as part of a bolus wizard feature of the client application 808 in lieu of presenting a GUI display for inputting carbohydrate counts. The meal size GUI display 1400 includes a list 1402 of GUI elements corresponding to different qualitative meal sizes, which are selectable by a user to input or otherwise indicate the size of the meal to be bolused. As described above, the patient's historical meal data and potentially other factors or data (e.g., time of day, day of week, geographic location, historical glycemic response, historical bolus dosages, and the like) may be utilized to convert the selected meal size indicated by the patient into a probable carbohydrate amount to be bolused for.

FIG. 15 depicts an activity GUI display 1500 that may be presented by the client application 808 on the computing device 806 to enable the patient to select or otherwise indicate activities he or she is likely to engage in within a postprandial period after administrating a bolus in connection with the patient activity control process 1300 of FIG. 13 after inputting a meal size using the meal size GUI display 1400. The activity GUI display 1500 includes a list 1502 of GUI elements corresponding to different activities that the patient may subsequently engage in that are likely to influence the patient's glycemic response or insulin sensitivity. As described above, the patient's historical meal, measurement, and delivery data associated with the selected activity and potentially other contextual factors may be analyzed to determine a probable glycemic response for the patient given the current operational context, which, in turn, may be utilized to adjust a calculated meal bolus amount or closed-loop control parameters to account for the patient's prospective postprandial activity. It should be noted that some embodiments of the patient activity control process 1300 and the activity GUI display 1500 may also be configured to support accounting for preprandial activities or other activities concurrent to or preceding a meal in an equivalent manner.

Figures 16, 17:
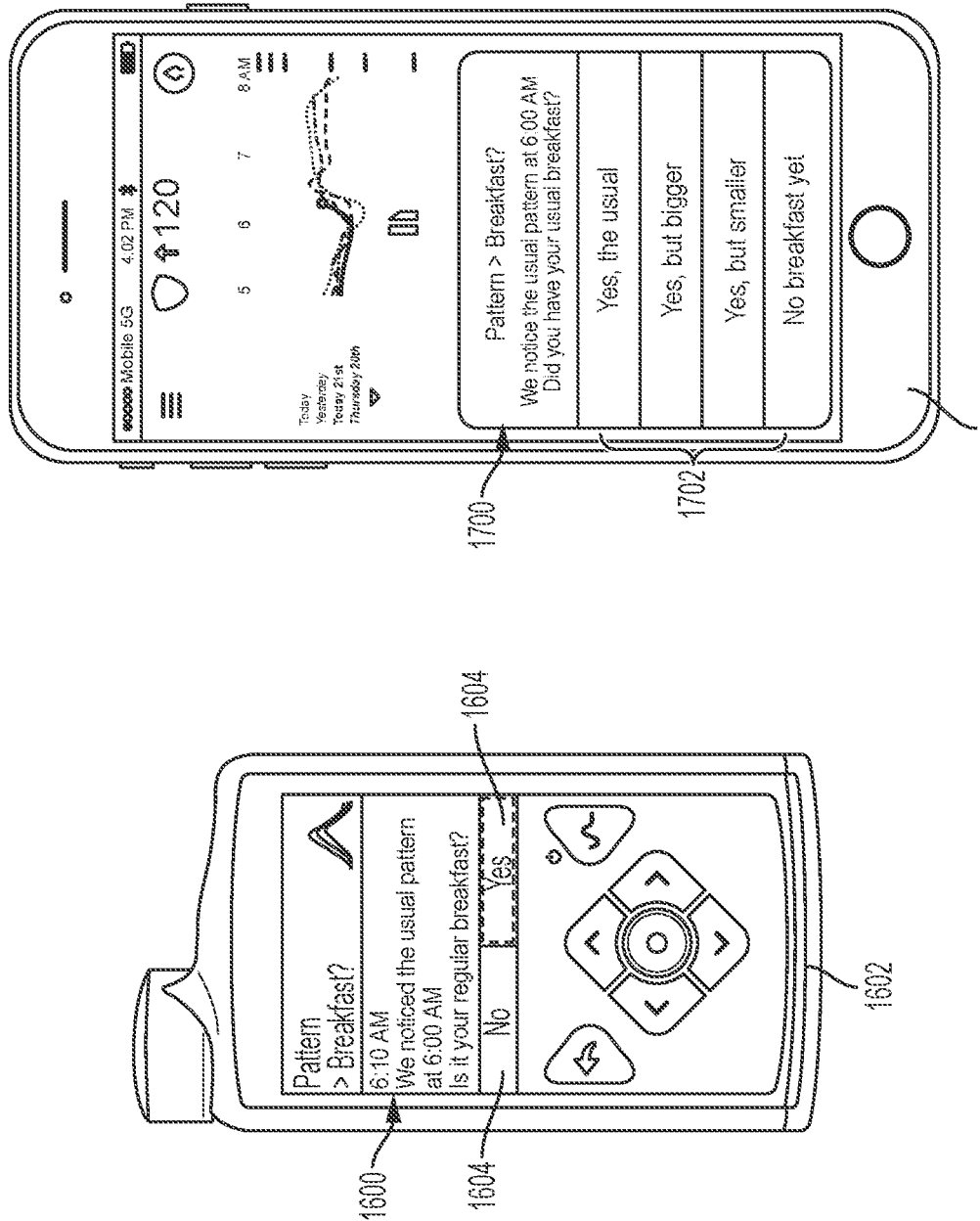
FIG. 16 depicts an exemplary graphical user interface display that may be presented on an infusion device in connection with the event pattern control process of FIG. 10.
FIG. 17 depicts an exemplary graphical user interface display that may be presented on a client computing device in connection with the event pattern control process of FIG. 10.

FIG. 16 depicts an exemplary GUI display 1600 that may be presented on a display device (e.g., display 226) associated with an infusion device 1602, such as any one of the infusion devices 102, 200, 502, 802 described above, in accordance with the event pattern control process 1000 of FIG. 10. For example, in response to detecting a pattern in the patient sensor glucose measurements that indicates that the patient has likely consumed breakfast based on the current time of day, the current day of the week, and/or potentially other factors with a relatively high enough probability, the personalization application 608 may generate or otherwise provide the GUI display 1600 to provide a graphical user notification that a breakfast pattern has been detected. The GUI display 1600 includes a notification region that includes textual information characterizing or describing the detected event pattern, along with GUI elements 1604 that are selectable by the patient to confirm or invalidate the detected activity. When patient selects a GUI element 1604 to confirm or validate the detected activity, the personalization application 608 may automatically adjust insulin delivery according to the patient's historical data and historical response to the detected activity given the current operational context as described above (e.g., task 1014).

FIG. 17 depicts an exemplary GUI display 1700 that may be presented on a display device associated with a client device 1706, such as any one of the client computing devices 106, 806 described above, in accordance with the event pattern control process 1000. Similar to the above example, in response to the client application 808 detecting a pattern in the patient's current or recent measurement data or other operational context information that indicates that the patient has likely consumed breakfast with a sufficiently great enough probability, the client application 808 may generate or otherwise provide the event pattern notification GUI display 1700 to graphically notify the patient that a breakfast pattern has been detected. The illustrated event pattern notification GUI display 1700 includes a list 1702 with a plurality of GUI elements that are selectable by the patient to confirm or invalidate the detected activity. The list 1702 also includes selectable GUI elements that allow the patient to confirm the detected activity but modify one or more attributes or characteristics of the activity relative to the patient's typical or usual activity given the current operational context. For example, in the illustrated embodiments, the GUI display 1700 includes selectable GUI elements that allow the patient to indicate whether a detected meal event pattern corresponds to a meal that deviates in size (or alternatively nutritional content or type) relative to the patient's typical meals at that time of day, day of week, etc. When patient selects a GUI element to confirm the detected activity but modify a characteristic or attribute thereof, the client application 808 may automatically adjust insulin delivery according to the patient's historical data and historical response to the detected activity given the current operational context in a manner that also accounts for the input modification by the patient, for example, by further adjusting the insulin delivery up or down based on whether the patient indicates the current meal is larger or smaller than normal for the current operational context.

Diabetes Data Management System Overview

Figure 18:
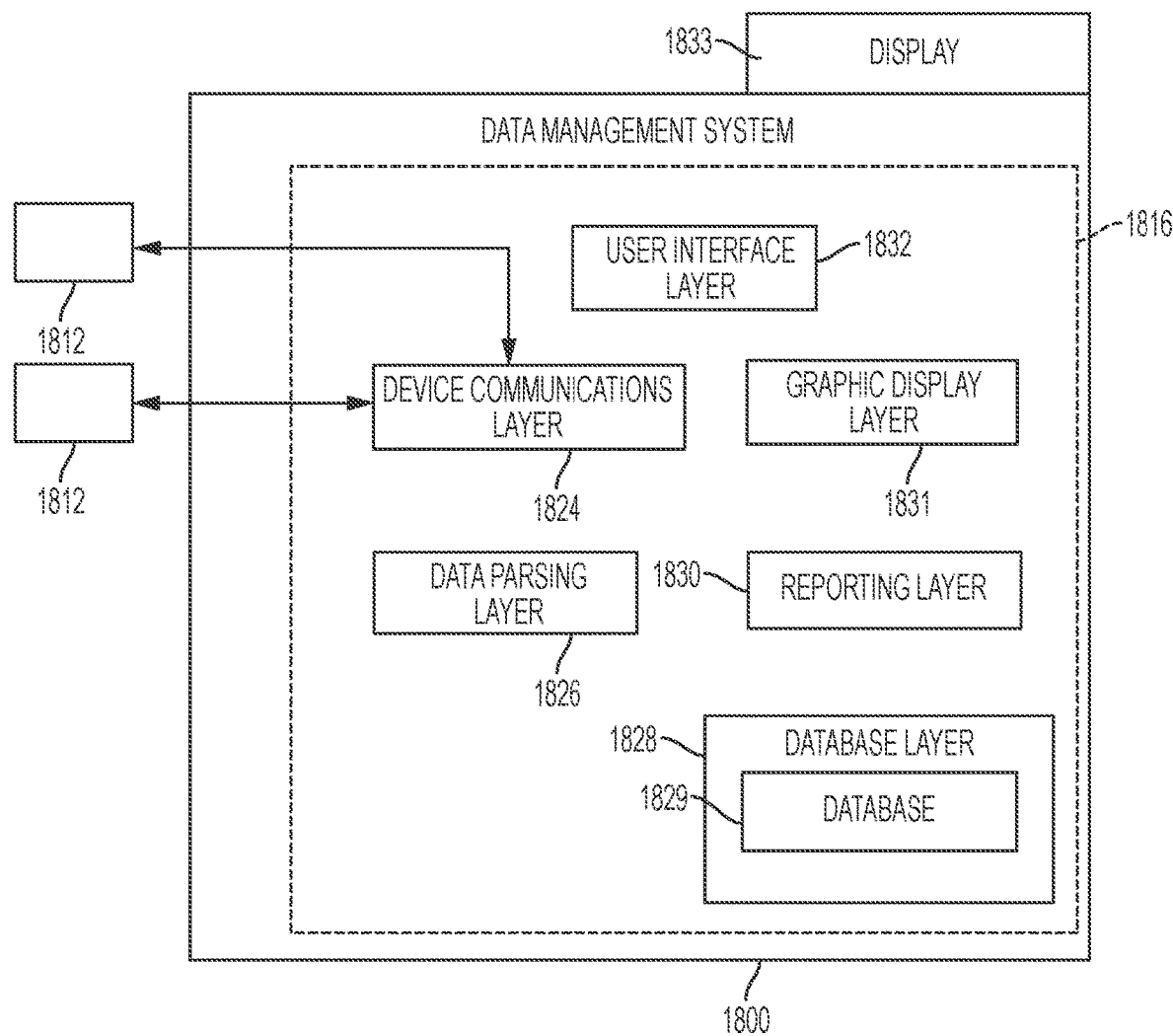
FIG. 18 depicts an embodiment of a computing device of a diabetes data management system suitable for use in connection with any one or more of the systems of FIGS. 1, 5 and 8 and any one or more of the processes of FIGS. 9-13 in accordance with one or more embodiments.

FIG. 18 illustrates a computing device 1800 suitable for use as part of a diabetes data management system in conjunction with one or more of the processes described above in the context of FIGS. 9-13. The diabetes data management system (DDMS) may be referred to as the Medtronic MiniMed CARELINK™ system or as a medical data management system (MDMS) in some embodiments. The DDMS may be housed on a server or a plurality of servers which a user or a health care professional may access via a communications network via the Internet or the World Wide Web. Some models of the DDMS, which is described as an MDMS, are described in U.S. Patent Application Publication Nos. 2006/0031094 and 2013/0338630, which is herein incorporated by reference in their entirety.

While description of embodiments are made in regard to monitoring medical or biological conditions for subjects having diabetes, the systems and processes herein are applicable to monitoring medical or biological conditions for cardiac subjects, cancer subjects, HIV subjects, subjects with other disease, infection, or controllable conditions, or various combinations thereof.

In embodiments of the invention, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 1800. The computing device 1800 may be coupled to a display 1833. In some embodiments, the computing device 1800 may be in a physical device separate from the display (such as in a personal computer, a mini-computer, etc.) In some embodiments, the computing device 1800 may be in a single physical enclosure or device with the display 1833 such as a laptop where the display 1833 is integrated into the computing device. In embodiments of the invention, the computing device 1800 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 1800 may also be a server located on the Internet that is accessible via a browser installed on a laptop computer, desktop computer, a network computer, or a PDA. The computing device 1800 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 18, the data management system 1816 comprises a group of interrelated software modules or layers that specialize in different tasks. The system software includes a device communication layer 1824, a data parsing layer 1826, a database layer 1828, database storage devices 1829, a reporting layer 1830, a graph display layer 1831, and a user interface layer 1832. The diabetes data management system may communicate with a plurality of subject support devices 1812, two of which are illustrated in FIG. 18. Although the different reference numerals refer to a number of layers, (e.g., a device communication layer, a data parsing layer, a database layer), each layer may include a single software module or a plurality of software modules. For example, the device communications layer 1824 may include a number of interacting software modules, libraries, etc. In embodiments of the invention, the data management system 1816 may be installed onto a non-volatile storage area (memory such as flash memory, hard disk, removable hard, DVD-RW, CD-RW) of the computing device 1800. If the data management system 1816 is selected or initiated, the system 1816 may be loaded into a volatile storage (memory such as DRAM, SRAM, RAM, DDRAM) for execution.

The device communication layer 1824 is responsible for interfacing with at least one, and, in further embodiments, to a plurality of different types of subject support devices 1812, such as, for example, blood glucose meters, glucose sensors/monitors, or an infusion pump. In one embodiment, the device communication layer 1824 may be configured to communicate with a single type of subject support device 1812. However, in more comprehensive embodiments, the device communication layer 1824 is configured to communicate with multiple different types of subject support devices 1812, such as devices made from multiple different manufacturers, multiple different models from a particular manufacturer and/or multiple different devices that provide different functions (such as infusion functions, sensing functions, metering functions, communication functions, user interface functions, or combinations thereof). By providing an ability to interface with multiple different types of subject support devices 1812, the diabetes data management system 1816 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 1824 allows the DDMS 1816 to receive information from and transmit information to or from each subject support device 1812 in the system 1816. Depending upon the embodiment and context of use, the type of information that may be communicated between the system 1816 and device 1812 may include, but is not limited to, data, programs, updated software, education materials, warning messages, notifications, device settings, therapy parameters, or the like. The device communication layer 1824 may include suitable routines for detecting the type of subject support device 1812 in communication with the system 1816 and implementing appropriate communication protocols for that type of device 1812. Alternatively or in addition, the subject support device 1812 may communicate information in packets or other data arrangements, where the communication includes a preamble or other portion that includes device identification information for identifying the type of the subject support device. Alternatively, or in addition, the subject support device 1812 may include suitable user-operable interfaces for allowing a user to enter information (e.g., by selecting an optional icon or text or other device identifier) that corresponds to the type of subject support device used by that user. Such information may be communicated to the system 1816, through a network connection. In yet further embodiments, the system 1816 may detect the type of subject support device 1812 it is communicating with in the manner described above and then may send a message requiring the user to verify that the system 1816 properly detected the type of subject support device being used by the user. For systems 1816 that are capable of communicating with multiple different types of subject support devices 1812, the device communication layer 1824 may be capable of implementing multiple different communication protocols and selects a protocol that is appropriate for the detected type of subject support device.

The data-parsing layer 1826 is responsible for validating the integrity of device data received and for inputting it correctly into a database 1829. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 1816 may compare received identification information with pre-stored information to evaluate whether the received information is from a valid source.

The database layer 1828 may include a centralized database repository that is responsible for warehousing and archiving stored data in an organized format for later access, and retrieval. The database layer 1828 operates with one or more data storage device(s) 1829 suitable for storing and providing access to data in the manner described herein. Such data storage device(s) 1829 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. Information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 1816 or other entities, for analyzing group data or other forms of conglomerate data.

Embodiments of the database layer 1828 and other components of the system 1816 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 1828 may be configured to limit access of each user to types of information pre-authorized for that user. For example, a subject may be allowed access to his or her individual medical information (with individual identifiers) stored by the database layer 1828, but not allowed access to other subject's individual medical information (with individual identifiers). Similarly, a subject's authorized healthcare provider or payor entity may be provided access to some or all of the subject's individual medical information (with individual identifiers) stored by the database layer 1828, but not allowed access to another individual's personal information. Also, an operator or administrator-user (on a separate computer communicating with the computing device 1800) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 1828 in the data storage devices 1829.

In exemplary embodiments, the database 1829 stores uploaded measurement data for a patient (e.g., sensor glucose measurement and characteristic impedance values) along with event log data consisting of event records created during a monitoring period corresponding to the measurement data. In embodiments of the invention, the database layer 1828 may also store preference profiles. In the database layer 1828, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 1829 in the database layer. Preference profiles may include various threshold values, monitoring period values, prioritization criteria, filtering criteria, and/or other user-specific values for parameters to generate a snapshot GUI display on the display 1833 or a support device 1812 in a personalized or patient-specific manner.

The DDMS 1816 may measure, analyze, and track either blood glucose (BG) or sensor glucose (SG) measurements (or readings) for a user. In embodiments of the invention, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 1830 may include a report wizard program that pulls data from selected locations in the database 1829 and generates report information from the desired parameters of interest. The reporting layer 1830 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar. In exemplary embodiments described herein, the reporting layer 1830 also facilitates generation of a snapshot report including a snapshot GUI display.

In embodiments of the invention, the database layer 1828 may calculate values for various medical information that is to be displayed on the reports generated by the report or reporting layer 1830. For example, the database layer 1828, may calculate average blood glucose or sensor glucose readings for specified timeframes. In embodiments of the invention, the reporting layer 1830 may calculate values for medical or physical information that is to be displayed on the reports. For example, a user may select parameters which are then utilized by the reporting layer 1830 to generate medical information values corresponding to the selected parameters. In other embodiments of the invention, the user may select a parameter profile that previously existed in the database layer 1828.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs. In this manner, users may import data from the system 1816 into further reporting tools familiar to the user. The reporting layer 1830 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 1830 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 1816 may allow a user generating a report to designate the report as non-printable and/or non-transferable, whereby the system 1816 will provide the report in a form that inhibits printing and/or electronic transfer.

The reporting layer 1830 may transfer selected reports to the graph display layer 1831. The graph display layer 1831 receives information regarding the selected reports and converts the data into a format that can be displayed or shown on a display 1833.

In embodiments of the invention, the reporting layer 1830 may store a number of the user's parameters. Illustratively, the reporting layer 1830 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 1832 supports interactions with the end user, for example, for user login and data access, software navigation, data input, user selection of desired report types and the display of selected information. Users may also input parameters to be utilized in the selected reports via the user interface layer 1832. Examples of users include but are not limited to: healthcare providers, healthcare payer entities, system operators or administrators, researchers, business entities, healthcare institutions and organizations, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 1832 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 1816, depending upon the embodiment of use.

In another example embodiment, where the DDMS 1816 is located on one computing device 1800, the user interface layer 1832 provides a number of menus to the user to navigate through the DDMS. These menus may be created utilizing any menu format, including but not limited to HTML, XML, or Active Server pages. A user may access the DDMS 1816 to perform one or more of a variety of tasks, such as accessing general information made available on a website to all subjects or groups of subjects. The user interface layer 1832 of the DDMS 1816 may allow a user to access specific information or to generate reports regarding that subject's medical condition or that subject's medical device(s) 1812, to transfer data or other information from that subject's support device(s) 1812 to the system 1816, to transfer data, programs, program updates or other information from the system 1816 to the subject's support device(s) 1812, to manually enter information into the system 1816, to engage in a remote consultation exchange with a healthcare provider, or to modify the custom settings in a subject's supported device and/or in a subject's DDMS/MDMS data file.

The system 1816 may provide access to different optional resources or activities (including accessing different information items and services) to different users and to different types or groups of users, such that each user may have a customized experience and/or each type or group of user (e.g., all users, diabetic users, cardio users, healthcare provider-user or payor-user, or the like) may have a different set of information items or services available on the system. The system 1816 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 1816, based on the type of user and/or the identity of the user.

Upon entering successful verification of the user's identification information and password, the user may be provided access to secure, personalized information stored on the DDMS 1816. For example, the user may be provided access to a secure, personalized location in the DDMS 1816 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 1812 to the system 1816, manually enter additional data into the system 1816, modify the subject's custom settings, and/or view and print reports. Reports may include data specific to the subject's condition, including but not limited to, data obtained from the subject's subject support device(s) 1812, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 1829) employed by the database layer 1828.

The user may select an option to transfer (send) device data to the medical data management system 1816. If the system 1816 receives a user's request to transfer device data to the system, the system 1816 may provide the user with step-by-step instructions on how to transfer data from the subject's supported device(s) 1812. For example, the DDMS 1816 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 1812 used by the subject. The system 1816 employs that information to select the stored instruction set(s) associated with the particular subject's support device(s) 1812 for display to the user.

Other activities or resources available to the user on the system 1816 may include an option for manually entering information to the DDMS/MDMS 1816. For example, from the user's personalized menu or location, the user may select an option to manually enter additional information into the system 1816.

Further optional activities or resources may be available to the user on the DDMS 1816. For example, from the user's personalized menu, the user may select an option to receive data, software, software updates, treatment recommendations or other information from the system 1816 on the subject's support device(s) 1812. If the system 1816 receives a request from a user to receive data, software, software updates, treatment recommendations or other information, the system 1816 may provide the user with a list or other arrangement of multiple selectable icons or other indicia representing available data, software, software updates or other information available to the user.

Yet further optional activities or resources may be available to the user on the medical data management system 1816 including, for example, an option for the user to customize or otherwise further personalize the user's personalized location or menu. In particular, from the user's personalized location, the user may select an option to customize parameters for the user. In addition, the user may create profiles of customizable parameters. When the system 1816 receives such a request from a user, the system 1816 may provide the user with a list or other arrangement of multiple selectable icons or other indicia representing parameters that may be modified to accommodate the user's preferences. When a user selects one or more of the icons or other indicia, the system 1816 may receive the user's request and makes the requested modification.

In one or more exemplary embodiments, for an individual patient in the DDMS, the computing device 1800 of the DDMS is configured to analyze that patient's historical measurement data, historical delivery data, historical event log data, and any other historical or contextual data associated with the patient maintained in the database layer 1828 to support one or more of the processes of FIGS. 9-13. In this regard, machine learning, artificial intelligence, or similar mathematical modeling of the patient's physiological behavior or response may be performed at the computing device 1800 to facilitate patient-specific correlations or predictions. Current measurement data, delivery data, and event log data associated with the patient along with current contextual data may be analyzed using the resultant models, either at the computing device 1800 of the DDMS or another device 1812 to determine probable events, behaviors, or responses by the patient in real-time and perform corresponding delivery adjustments in a manner that is influenced by a correlative subset of the patient's historical data. As a result, patient outcomes may be improved while reducing the burden on the patient to make such patient-specific adjustments.

For the sake of brevity, conventional techniques related to glucose sensing and/or monitoring, sensor calibration and/or compensation, bolusing, machine learning and/or artificial intelligence, pharmodynamic modeling, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating a medical device capable of delivering a fluid to a patient, the method comprising:
    obtaining historical data associated with a meal size for the patient;
    determining, by a control system associated with the medical device, an estimated carbohydrate ratio associated with the meal size for a meal based at least in part on the historical data associated with the meal size;
    determining, by the control system, a bolus dosage of the fluid based at least in part on the estimated carbohydrate ratio and an estimated carbohydrate amount corresponding to the meal size; and
    operating, by the control system, the medical device to deliver the bolus dosage of the fluid to the patient.

2. The method of claim 1, wherein determining the estimated carbohydrate ratio comprises determining the estimated carbohydrate ratio associated with the meal size based at least in part on the historical data and a current time of day.

3. The method of claim 1, wherein determining the estimated carbohydrate ratio comprises identifying the estimated carbohydrate ratio for the meal size that results in an estimated postprandial peak sensor glucose value at an estimated postprandial peak time following a meal event equal to a desired target postprandial peak sensor glucose value.

4. The method of claim 3, wherein identifying the estimated carbohydrate ratio comprises optimizing a mathematical model of a response by the patient to meals having the meal size.

5. The method of claim 1, wherein determining the estimated carbohydrate ratio comprises identifying a carbohydrate ratio for the meal size that is likely to achieve a desired postprandial response based on the historical data.

6. The method of claim 1, wherein:
    the meal size comprises an input qualitative meal size; and
    the estimated carbohydrate ratio comprises a patient-specific carbohydrate amount associated with the input qualitative meal size that accounts for variability associated with the input qualitative meal size.

7. The method of claim 1, wherein:
    the meal size comprises an input qualitative meal size;
    the historical data includes historical carbohydrate amounts associated with historical meal events for the patient associated with the input qualitative meal size; and
    the method further comprises determining the estimated carbohydrate amount corresponding to the input qualitative meal size based at least in part on the historical carbohydrate amounts.

8. The method of claim 7, further comprising presenting a graphical user interface (GUI) display including a list of GUI elements corresponding to different qualitative meal sizes, wherein at least one of the GUI elements is selectable by a user to indicate the input qualitative meal size.

9. The method of claim 8, wherein the different qualitative meal sizes include small, medium, and large.

10. The method of claim 1, further comprising:
    obtaining an indication of nutritional content of the meal; and
    determining the estimated carbohydrate amount based at least in part on historical carbohydrate amounts associated with historical meal events including the nutritional content.

11. The method of claim 10, wherein determining the bolus dosage comprises:
    calculating an initial bolus dosage based at least in part on the estimated carbohydrate amount; and
    adjusting the initial bolus dosage based on the nutritional content to obtain the bolus dosage.

12. The method of claim 11 wherein adjusting the initial bolus dosage comprises decreasing the initial bolus dosage when the nutritional content indicates a relatively high fat meal.

13. The method of claim 11, wherein adjusting the initial bolus dosage comprises increasing the initial bolus dosage when the nutritional content indicates a relatively high carbohydrate meal.

14. The method of claim 10, further comprising adjusting a closed-loop control parameter based on the nutritional content.

15. The method of claim 10, further comprising temporarily suspending delivery of the fluid by a closed-loop control system of the medical device based on the nutritional content.

16. A non-transitory computer-readable medium having instructions stored thereon that, when executed by a processor, cause the processor to:
    obtain historical data associated with a meal size for a patient;
    determine an estimated carbohydrate ratio associated with the meal size for a meal based at least in part on the historical data associated with the meal size;
    determine a bolus dosage of fluid based at least in part on the estimated carbohydrate ratio and an estimated carbohydrate amount corresponding to the meal size; and
    operate a medical device to deliver the bolus dosage of the fluid to the patient.

17. The non-transitory computer-readable medium of claim 16, wherein the meal size comprises an input qualitative meal size.

18. The non-transitory computer-readable medium of claim 17, wherein the instructions cause the processor to present a graphical user interface (GUI) display including a list of GUI elements corresponding to different qualitative meal sizes that are selectable by a user to indicate the input qualitative meal size.

19. The non-transitory computer-readable medium of claim 16, wherein the instructions cause the processor to identify the estimated carbohydrate ratio for the meal size that results in an estimated postprandial peak sensor glucose value at an estimated postprandial peak time following a meal event equal to a desired target postprandial peak sensor glucose value.

20. A device comprising:
    a data storage element having executable instructions stored thereon; and
    a processing system coupled to the data storage element, wherein the executable instructions cause the processing system to:

obtain historical data associated with historical meal events associated with a meal size for a patient;

determine an estimated carbohydrate ratio associated with the meal size based at least in part on the historical data;

determine a bolus dosage of a fluid based at least in part on the estimated carbohydrate ratio and an estimated carbohydrate amount corresponding to the meal size; and operate a medical device to deliver the bolus dosage of the fluid to the patient.

* * * * *